(12) United States Patent
Vidlund et al.

(10) Patent No.: US 11,298,227 B2
(45) Date of Patent: Apr. 12, 2022

(54) TRICUSPID REGURGITATION CONTROL DEVICES FOR ORTHOGONAL TRANSCATHETER HEART VALVE PROSTHESIS

(71) Applicant: VDyne, Inc., Maple Grove, MN (US)

(72) Inventors: Robert Vidlund, Forest Lake, MN (US); Mark Christianson, Plymouth, MN (US); Neelakantan Saikrishnan, Plymouth, MN (US)

(73) Assignee: VDyne, Inc., Maple Grove, MN (US)

( * ) Notice: Subject to any disclaimer, the term of this patent is extended or adjusted under 35 U.S.C. 154(b) by 0 days.

(21) Appl. No.: 17/222,430

(22) Filed: Apr. 5, 2021

(65) Prior Publication Data
US 2021/0315694 A1    Oct. 14, 2021

Related U.S. Application Data

(63) Continuation of application No. PCT/US2020/021300, filed on Mar. 4, 2020.
(Continued)

(51) Int. Cl.
*A61F 2/24* (2006.01)
*A61N 1/375* (2006.01)
*A61N 1/05* (2006.01)

(52) U.S. Cl.
CPC .......... *A61F 2/2424* (2013.01); *A61F 2/2403* (2013.01); *A61F 2/2409* (2013.01);
(Continued)

(58) Field of Classification Search
CPC ........................................................ A61F 2/24
See application file for complete search history.

(56) References Cited

U.S. PATENT DOCUMENTS 3,744,060 A * 7/1973 Bellhouse ............. A61F 2/2409
  623/2.1
4,079,468 A * 3/1978 Liotta ................... A61F 2/2409
  623/2.17
(Continued)

FOREIGN PATENT DOCUMENTS

AU     2006203686 B2    11/2008
AU     2009219415 A1     9/2009
(Continued)

OTHER PUBLICATIONS

International Search Report and Written Opinion for International Application No. PCT/US2019/028822, dated Oct. 24, 2019, 14 pages.
(Continued)

*Primary Examiner* — Jacqueline Wozniki

(57) ABSTRACT

The invention relates to a heart valve regurgitation drum and optional closure disk and/or tubular stent to manage and provide levels of intentional regurgitation within an orthogonally delivered transcatheter prosthetic heart valve having a first inner flow control component/valve, a second inner regurgitation control component, and an outer annular support frame having compressible wire cells that facilitate folding flat along the z-axis and compressing the valve vertically along the y-axis, or orthogonally to the central axis of the flow control component, allowing a very large diameter valve to be delivered and deployed to the tricuspid valve from the inferior vena cava or superior vena cava, or trans-atrially to the mitral valve, the valve having a height of about 5-60 mm and a diameter of about 25-80 mm, without requiring an oversized diameter catheter and without requiring delivery and deployment from a catheter at an acute angle of approach.

8 Claims, 22 Drawing Sheets

Related U.S. Application Data

(60) Provisional application No. 62/813,770, filed on Mar. 5, 2019.

(52) U.S. Cl.
CPC .......... *A61F 2/2412* (2013.01); *A61N 1/0587* (2013.01); *A61N 1/37512* (2017.08); *A61F 2210/0014* (2013.01); *A61F 2250/0098* (2013.01)

(56) References Cited

U.S. PATENT DOCUMENTS

| | | | |
|---|---|---|---|
| 5,397,351 A | 3/1995 | Pavcnik et al. | |
| 5,509,428 A | 4/1996 | Dunlop | |
| 5,554,185 A | 9/1996 | Block et al. | |
| 6,006,134 A | 12/1999 | Hill et al. | |
| 6,197,013 B1 | 3/2001 | Reed et al. | |
| 6,290,719 B1 | 9/2001 | Garberoglio | |
| 6,312,464 B1 | 11/2001 | Navia | |
| 6,449,507 B1 | 9/2002 | Hill et al. | |
| 6,458,153 B1* | 10/2002 | Bailey | A61F 2/07 623/1.24 |
| 6,532,388 B1 | 3/2003 | Hill et al. | |
| 6,582,467 B1 | 6/2003 | Teitelbaum et al. | |
| 6,628,987 B1 | 9/2003 | Hill et al. | |
| 6,669,724 B2* | 12/2003 | Park | A61F 2/2418 623/1.24 |
| 6,718,208 B2 | 4/2004 | Hill et al. | |
| 6,769,434 B2 | 8/2004 | Liddicoat et al. | |
| 6,890,330 B2 | 5/2005 | Streeter et al. | |
| 6,896,690 B1 | 5/2005 | Lambrecht et al. | |
| 6,904,318 B2 | 6/2005 | Hill et al. | |
| 6,929,653 B2 | 8/2005 | Strecter | |
| 7,074,189 B1 | 7/2006 | Montegrande | |
| 7,125,418 B2 | 10/2006 | Duran et al. | |
| 7,175,660 B2 | 2/2007 | Cartledge et al. | |
| 7,201,761 B2 | 4/2007 | Woolfson et al. | |
| 7,225,019 B2 | 5/2007 | Jahns et al. | |
| 7,269,457 B2 | 9/2007 | Shafer et al. | |
| 7,331,991 B2 | 2/2008 | Kheradvar et al. | |
| 7,361,189 B2* | 4/2008 | Case | A61F 2/2412 623/1.24 |
| 7,374,571 B2 | 5/2008 | Pease et al. | |
| 7,442,204 B2* | 10/2008 | Schwammenthal | A61F 2/2418 623/1.24 |
| 7,449,027 B2 | 11/2008 | Hunt et al. | |
| 7,621,948 B2 | 11/2009 | Herrmann et al. | |
| 7,648,527 B2* | 1/2010 | Agnew | A61F 2/2475 623/1.24 |
| 7,717,952 B2 | 5/2010 | Case et al. | |
| 7,749,245 B2 | 7/2010 | Cohn et al. | |
| 7,753,949 B2 | 7/2010 | Lamphere et al. | |
| 7,811,316 B2* | 10/2010 | Kalmann | A61F 2/2475 623/1.24 |
| 7,828,840 B2 | 11/2010 | Biggs et al. | |
| 7,846,199 B2 | 12/2010 | Paul, Jr. et al. | |
| 8,303,648 B2 | 11/2012 | Grewe et al. | |
| 8,366,768 B2 | 2/2013 | Zhang | |
| 8,491,650 B2 | 7/2013 | Wiemeyer et al. | |
| 8,568,474 B2 | 10/2013 | Yeung et al. | |
| 8,628,571 B1* | 1/2014 | Hacohen | A61F 2/2403 623/2.2 |
| 8,641,752 B1 | 2/2014 | Holm et al. | |
| 8,696,743 B2 | 4/2014 | Holecek et al. | |
| 8,728,153 B2 | 5/2014 | Bishop et al. | |
| 8,758,395 B2 | 6/2014 | Kleshinski et al. | |
| 8,846,390 B2 | 9/2014 | Dove et al. | |
| 8,876,892 B2 | 11/2014 | Tran et al. | |
| 8,900,295 B2 | 12/2014 | Migliazza et al. | |
| 8,915,958 B2 | 12/2014 | Braido | |
| 8,926,690 B2 | 1/2015 | Kovalsky | |
| 8,926,692 B2 | 1/2015 | Dwork | |
| 8,926,694 B2 | 1/2015 | Costello | |
| 8,940,044 B2 | 1/2015 | Hammer et al. | |
| 8,956,404 B2 | 2/2015 | Bortlein et al. | |
| 8,986,370 B2 | 3/2015 | Annest et al. | |
| 9,011,524 B2 | 4/2015 | Eberhardt | |
| 9,017,399 B2 | 4/2015 | Gross et al. | |
| 9,050,188 B2 | 6/2015 | Schweich, Jr. et al. | |
| 9,072,604 B1 | 7/2015 | Melnick et al. | |
| 9,119,714 B2 | 9/2015 | Shandas et al. | |
| 9,216,076 B2 | 12/2015 | Mitra et al. | |
| 9,232,995 B2 | 1/2016 | Kovalsky et al. | |
| 9,241,792 B2 | 1/2016 | Benichou et al. | |
| 9,248,016 B2 | 2/2016 | Oba et al. | |
| 9,259,215 B2 | 2/2016 | Chou et al. | |
| 9,277,990 B2 | 3/2016 | Klima et al. | |
| 9,289,282 B2 | 3/2016 | Olson et al. | |
| 9,289,296 B2 | 3/2016 | Braido et al. | |
| 9,295,547 B2 | 3/2016 | Costello et al. | |
| 9,301,839 B2 | 4/2016 | Stante et al. | |
| 9,308,086 B2 | 4/2016 | Ho | |
| 9,339,367 B2 | 5/2016 | Carpenter et al. | |
| 9,370,418 B2 | 6/2016 | Pintor et al. | |
| 9,381,083 B2 | 7/2016 | Costello | |
| 9,387,075 B2 | 7/2016 | Bortlein et al. | |
| 9,393,111 B2 | 7/2016 | Ma et al. | |
| 9,414,915 B2 | 8/2016 | Lombardi et al. | |
| 9,433,500 B2 | 9/2016 | Chau et al. | |
| 9,440,054 B2 | 9/2016 | Bishop et al. | |
| 9,456,899 B2 | 10/2016 | Yeung et al. | |
| 9,468,525 B2 | 10/2016 | Kovalsky et al. | |
| 9,474,604 B2 | 10/2016 | Centola et al. | |
| 9,486,306 B2 | 11/2016 | Tegels et al. | |
| 9,510,941 B2 | 12/2016 | Bishop et al. | |
| 9,554,902 B2 | 1/2017 | Braido et al. | |
| 9,579,196 B2 | 2/2017 | Morriss et al. | |
| 9,579,200 B2 | 2/2017 | Lederman et al. | |
| 9,597,181 B2 | 3/2017 | Christianson et al. | |
| 9,610,159 B2 | 4/2017 | Christianson et al. | |
| 9,615,925 B2 | 4/2017 | Subramanian et al. | |
| 9,629,719 B2 | 4/2017 | Rothstein | |
| 9,636,222 B2 | 5/2017 | Oslund | |
| 9,649,191 B2 | 5/2017 | Savage et al. | |
| 9,662,202 B2 | 5/2017 | Quill et al. | |
| 9,662,203 B2 | 5/2017 | Sheahan et al. | |
| 9,662,209 B2 | 5/2017 | Gross et al. | |
| 9,675,454 B2 | 6/2017 | Vidlund et al. | |
| 9,675,485 B2 | 6/2017 | Essinger et al. | |
| 9,687,343 B2 | 6/2017 | Bortlein et al. | |
| 9,707,076 B2 | 7/2017 | Stack et al. | |
| 9,713,530 B2 | 7/2017 | Cabiri et al. | |
| 9,750,607 B2 | 9/2017 | Ganesan et al. | |
| 9,763,778 B2 | 9/2017 | Eidenschink et al. | |
| 9,763,779 B2 | 9/2017 | Bortlein et al. | |
| 9,788,946 B2 | 10/2017 | Bobo, Jr. et al. | |
| 9,839,511 B2 | 12/2017 | Ma et al. | |
| 9,849,011 B2 | 12/2017 | Zimmerman et al. | |
| 9,855,384 B2 | 1/2018 | Cohen et al. | |
| 9,861,464 B2 | 1/2018 | Azimpour et al. | |
| 9,895,219 B2 | 2/2018 | Costello et al. | |
| 9,901,330 B2 | 2/2018 | Akpinar | |
| 9,918,838 B2 | 3/2018 | Ring | |
| 9,943,409 B2 | 4/2018 | Kim et al. | |
| 9,949,825 B2 | 4/2018 | Braido et al. | |
| 9,968,444 B2 | 5/2018 | Millwee et al. | |
| 9,968,445 B2 | 5/2018 | Kheradvar | |
| 9,980,815 B2 | 5/2018 | Nitzan et al. | |
| 9,987,121 B2 | 6/2018 | Blanzy | |
| 10,010,411 B2 | 7/2018 | Peter | |
| 10,010,412 B2 | 7/2018 | Taft et al. | |
| 10,022,054 B2 | 7/2018 | Najafi et al. | |
| 10,022,222 B2 | 7/2018 | Groothuis et al. | |
| 10,022,223 B2 | 7/2018 | Bruchman | |
| 10,028,821 B2 | 7/2018 | Centola et al. | |
| 10,028,831 B2 | 7/2018 | Morin et al. | |
| 10,034,667 B2 | 7/2018 | Morris et al. | |
| 10,034,747 B2 | 7/2018 | Harewood | |
| 10,039,638 B2 | 8/2018 | Bruchman et al. | |
| 10,058,315 B2 | 8/2018 | Rafiee et al. | |
| 10,058,411 B2 | 8/2018 | Fifer et al. | |
| 10,058,421 B2 | 8/2018 | Eberhardt et al. | |
| 10,058,426 B2 | 8/2018 | Barbarino | |

(56) References Cited

U.S. PATENT DOCUMENTS

| | | | |
|---|---|---|---|
| 10,064,405 B2 | 9/2018 | Dale et al. | |
| 10,080,653 B2 | 9/2018 | Conklin et al. | |
| 10,085,835 B2 | 10/2018 | Thambar et al. | |
| 10,105,224 B2 | 10/2018 | Buchbinder et al. | |
| 10,117,741 B2 | 11/2018 | Schweich, Jr. et al. | |
| 10,123,874 B2 | 11/2018 | Khairkhahan et al. | |
| 10,130,331 B2 | 11/2018 | Stigall et al. | |
| 10,130,467 B2 | 11/2018 | Braido et al. | |
| 10,149,685 B2 | 12/2018 | Kizuka | |
| 10,154,905 B2 | 12/2018 | Duffy | |
| 10,179,043 B2 | 1/2019 | Cohen-Tzemach et al. | |
| 10,182,908 B2 | 1/2019 | Tubishevitz et al. | |
| 10,182,911 B2 | 1/2019 | Hillukka | |
| 10,206,775 B2 | 2/2019 | Kovalsky et al. | |
| 10,219,895 B2 | 3/2019 | Wagner et al. | |
| 10,219,896 B2 | 3/2019 | Sandstrom et al. | |
| 10,220,192 B2 | 3/2019 | Drasler et al. | |
| 10,226,178 B2 | 3/2019 | Cohen et al. | |
| 10,226,335 B2 | 3/2019 | Cartledge et al. | |
| 10,245,142 B2 | 4/2019 | Bonhoeffer | |
| 10,258,467 B2 | 4/2019 | Hou et al. | |
| 10,265,173 B2 | 4/2019 | Griffin et al. | |
| 10,321,987 B2 | 6/2019 | Wang et al. | |
| 10,321,995 B1 | 6/2019 | Christianson et al. | |
| 10,327,895 B2 | 6/2019 | Lozonschi et al. | |
| 10,327,899 B2 | 6/2019 | Sandstrom et al. | |
| 10,329,066 B2 | 6/2019 | Kruetzfeldt et al. | |
| 10,350,047 B2 | 7/2019 | Rajpara et al. | |
| 10,357,361 B2 | 7/2019 | Rafi et al. | |
| 10,368,989 B2 | 8/2019 | Duffy et al. | |
| 10,398,550 B2 | 9/2019 | Chalekian et al. | |
| 10,426,611 B2 | 10/2019 | Hariton et al. | |
| 10,433,957 B2 | 10/2019 | Khouengboua et al. | |
| 10,433,960 B1 | 10/2019 | Sutherland et al. | |
| 10,463,489 B2 | 11/2019 | Christianson et al. | |
| 10,485,976 B2 | 11/2019 | Streeter et al. | |
| 10,595,994 B1* | 3/2020 | Christianson | A61F 2/2436 |
| 10,631,983 B1* | 4/2020 | Christianson | A61F 2/243 |
| 10,653,522 B1* | 5/2020 | Vidlund | A61F 2/2433 |
| 10,758,346 B1* | 9/2020 | Christianson | A61F 2/2418 |
| 10,761,511 B2 | 9/2020 | Chen et al. | |
| 10,779,937 B2 | 9/2020 | Vidlund et al. | |
| 11,071,627 B2 | 7/2021 | Saikrishnan et al. | |
| 11,076,956 B2 | 8/2021 | Christianson et al. | |
| 11,109,969 B2 | 9/2021 | Vidlund et al. | |
| 11,166,814 B2 | 11/2021 | Vidlund et al. | |
| 11,173,027 B2 | 11/2021 | Christianson et al. | |
| 11,179,239 B2 | 11/2021 | Vidlund et al. | |
| 11,185,409 B2 | 11/2021 | Christianson et al. | |
| 11,202,706 B2 | 12/2021 | Christianson et al. | |
| 2003/0040772 A1 | 2/2003 | Hyodoh et al. | |
| 2003/0040808 A1* | 2/2003 | Stack | A61F 5/0089 623/23.65 |
| 2003/0153901 A1 | 8/2003 | Herweck et al. | |
| 2003/0166990 A1 | 9/2003 | Trauthen et al. | |
| 2003/0171801 A1 | 9/2003 | Bates | |
| 2004/0049207 A1* | 3/2004 | Goldfarb | A61B 17/08 606/139 |
| 2004/0088047 A1 | 5/2004 | Spence et al. | |
| 2004/0093060 A1* | 5/2004 | Seguin | A61F 2/2418 623/1.11 |
| 2004/0116996 A1 | 6/2004 | Freitag | |
| 2004/0199209 A1 | 10/2004 | Hill et al. | |
| 2004/0225352 A1* | 11/2004 | Osborne | A61F 2/2418 623/1.24 |
| 2005/0010246 A1 | 1/2005 | Streeter et al. | |
| 2005/0075659 A1* | 4/2005 | Realyvasquez | A61B 17/0682 606/167 |
| 2005/0075725 A1* | 4/2005 | Rowe | A61F 2/844 623/2.14 |
| 2005/0107811 A1 | 5/2005 | Starksen et al. | |
| 2005/0137686 A1 | 6/2005 | Salahieh et al. | |
| 2005/0228495 A1* | 10/2005 | Macoviak | A61F 2/2415 623/2.18 |
| 2006/0015167 A1 | 1/2006 | Armstrong et al. | |
| 2006/0190075 A1 | 8/2006 | Jordan et al. | |
| 2006/0195180 A1 | 8/2006 | Kheradvar et al. | |
| 2006/0229708 A1* | 10/2006 | Powell | A61F 2/246 623/1.24 |
| 2006/0241745 A1* | 10/2006 | Solem | A61F 2/2442 623/2.18 |
| 2006/0271098 A1 | 11/2006 | Peacock, III | |
| 2006/0276887 A1 | 12/2006 | Brady et al. | |
| 2007/0016286 A1 | 1/2007 | Herrmann et al. | |
| 2007/0027535 A1 | 2/2007 | Purdy, Jr. et al. | |
| 2007/0032850 A1 | 2/2007 | Ruiz et al. | |
| 2007/0038295 A1 | 2/2007 | Case et al. | |
| 2007/0100427 A1 | 5/2007 | Perouse | |
| 2007/0162102 A1 | 7/2007 | Ryan et al. | |
| 2007/0208417 A1 | 9/2007 | Agnew | |
| 2007/0213805 A1 | 9/2007 | Schaeffer et al. | |
| 2007/0233176 A1 | 10/2007 | Gilson et al. | |
| 2007/0233228 A1 | 10/2007 | Eberhardt et al. | |
| 2007/0239271 A1 | 10/2007 | Nguyen | |
| 2007/0288087 A1 | 12/2007 | Fearnot et al. | |
| 2008/0004686 A1 | 1/2008 | Hunt et al. | |
| 2008/0020013 A1 | 1/2008 | Reyes et al. | |
| 2008/0065204 A1* | 3/2008 | Macoviak | A61F 2/2445 623/2.17 |
| 2008/0071287 A1 | 3/2008 | Goto | |
| 2008/0132999 A1 | 6/2008 | Mericle et al. | |
| 2008/0140181 A1 | 6/2008 | Reynolds et al. | |
| 2008/0154355 A1* | 6/2008 | Benichou | A61F 2/2412 623/1.26 |
| 2008/0183279 A1* | 7/2008 | Bailey | A61F 2/2412 623/1.24 |
| 2008/0200977 A1 | 8/2008 | Paul et al. | |
| 2008/0200980 A1 | 8/2008 | Robin et al. | |
| 2008/0208332 A1 | 8/2008 | Lamphere et al. | |
| 2008/0221672 A1 | 9/2008 | Lamphere et al. | |
| 2008/0262592 A1 | 10/2008 | Jordan et al. | |
| 2008/0262609 A1 | 10/2008 | Gross et al. | |
| 2008/0275550 A1 | 11/2008 | Kheradvar et al. | |
| 2009/0005863 A1 | 1/2009 | Goetz et al. | |
| 2009/0054976 A1 | 2/2009 | Tuval et al. | |
| 2009/0094189 A1 | 4/2009 | Stephens | |
| 2009/0192586 A1 | 7/2009 | Tabor et al. | |
| 2009/0254174 A1 | 10/2009 | Case et al. | |
| 2009/0264991 A1 | 10/2009 | Paul, Jr. et al. | |
| 2009/0287290 A1 | 11/2009 | MacAulay et al. | |
| 2010/0049294 A1 | 2/2010 | Zukowski et al. | |
| 2010/0049313 A1 | 2/2010 | Alon et al. | |
| 2010/0087918 A1 | 4/2010 | Vesely et al. | |
| 2010/0121434 A1 | 5/2010 | Paul et al. | |
| 2010/0160773 A1 | 6/2010 | Cohen et al. | |
| 2010/0161043 A1 | 6/2010 | Maisano et al. | |
| 2010/0168844 A1 | 7/2010 | Toomes et al. | |
| 2010/0174363 A1 | 7/2010 | Castro | |
| 2010/0179583 A1 | 7/2010 | Carpenter et al. | |
| 2010/0179584 A1 | 7/2010 | Carpenter et al. | |
| 2010/0179647 A1 | 7/2010 | Carpenter et al. | |
| 2010/0280591 A1 | 11/2010 | Shin et al. | |
| 2010/0298929 A1* | 11/2010 | Thornton | A61F 2/2445 623/2.1 |
| 2010/0305685 A1 | 12/2010 | Millwee et al. | |
| 2011/0004237 A1* | 1/2011 | Schneider | A61F 2/86 606/194 |
| 2011/0029071 A1 | 2/2011 | Zlotnick et al. | |
| 2011/0029072 A1* | 2/2011 | Gabbay | A61F 2/2418 623/2.23 |
| 2011/0066233 A1* | 3/2011 | Thornton | A61B 17/00234 623/2.11 |
| 2011/0071613 A1 | 3/2011 | Wood et al. | |
| 2011/0098804 A1 | 4/2011 | Yeung et al. | |
| 2011/0125145 A1 | 5/2011 | Mody et al. | |
| 2011/0137397 A1* | 6/2011 | Chau | A61F 2/246 623/1.11 |
| 2011/0160836 A1 | 6/2011 | Behan | |
| 2011/0172764 A1 | 7/2011 | Badhwar | |
| 2011/0224785 A1 | 9/2011 | Hacohen et al. | |
| 2011/0245911 A1* | 10/2011 | Quill | A61F 2/2418 623/1.26 |

(56) References Cited

U.S. PATENT DOCUMENTS

| | | |
|---|---|---|
| 2011/0245917 A1 | 10/2011 | Savage et al. |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson et al. |
| 2012/0022639 A1* | 1/2012 | Hacohen ............ A61F 2/2439 623/2.11 |
| 2012/0022640 A1 | 1/2012 | Gross et al. |
| 2012/0022644 A1 | 1/2012 | Reich et al. |
| 2012/0035701 A1 | 2/2012 | To |
| 2012/0065723 A1 | 3/2012 | Drasler et al. |
| 2012/0083874 A1 | 4/2012 | Dale et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim et al. |
| 2012/0277853 A1 | 11/2012 | Rothstein |
| 2012/0310327 A1 | 12/2012 | McHugo |
| 2012/0310328 A1* | 12/2012 | Olson ............ A61F 2/2469 623/1.26 |
| 2013/0035759 A1* | 2/2013 | Gross ............ A61F 2/2418 623/2.38 |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge et al. |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1* | 10/2013 | Schweich, Jr. ....... A61F 2/2412 623/2.11 |
| 2013/0297010 A1 | 11/2013 | Bishop et al. |
| 2013/0304197 A1* | 11/2013 | Buchbinder ......... A61F 2/2418 623/2.11 |
| 2013/0304200 A1* | 11/2013 | McLean ............ A61F 2/2436 623/2.18 |
| 2013/0331929 A1 | 12/2013 | Mitra et al. |
| 2013/0338764 A1* | 12/2013 | Thornton ........... A61B 17/0401 623/2.11 |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0005778 A1* | 1/2014 | Buchbinder ......... A61F 2/2412 623/2.18 |
| 2014/0012372 A1 | 1/2014 | Chau et al. |
| 2014/0018915 A1 | 1/2014 | Baidillah et al. |
| 2014/0039511 A1 | 2/2014 | Morris et al. |
| 2014/0039611 A1 | 2/2014 | Lane et al. |
| 2014/0052237 A1* | 2/2014 | Lane ............ A61F 2/2418 623/2.11 |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0135908 A1* | 5/2014 | Glozman ............ A61F 2/2418 623/2.11 |
| 2014/0142695 A1 | 5/2014 | Gross et al. |
| 2014/0172070 A1 | 6/2014 | Seguin |
| 2014/0180069 A1 | 6/2014 | Millett |
| 2014/0180070 A1 | 6/2014 | Millett et al. |
| 2014/0194704 A1 | 7/2014 | Millett et al. |
| 2014/0194983 A1* | 7/2014 | Kovalsky ............ A61F 2/2418 623/2.38 |
| 2014/0207231 A1* | 7/2014 | Hacohen ............ A61F 2/2436 623/2.11 |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0249566 A1 | 9/2014 | Quinn et al. |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0296962 A1 | 10/2014 | Cartledge et al. |
| 2014/0296969 A1 | 10/2014 | Tegels et al. |
| 2014/0296975 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0350662 A1* | 11/2014 | Vaturi ............ A61F 2/2445 623/2.1 |
| 2014/0358224 A1* | 12/2014 | Tegels ............ A61F 2/2418 623/2.14 |
| 2014/0371789 A1 | 12/2014 | Hariton et al. |
| 2014/0379076 A1 | 12/2014 | Vidlund et al. |
| 2015/0005808 A1 | 1/2015 | Chouinard et al. |
| 2015/0005874 A1 | 1/2015 | Vidlund et al. |
| 2015/0039081 A1 | 2/2015 | Costello |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1* | 8/2015 | Hacohen ............ A61B 17/0401 623/2.37 |
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1* | 12/2015 | Hammer ............ A61F 2/2409 623/2.11 |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038280 A1 | 2/2016 | Morriss et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |

(56) References Cited

U.S. PATENT DOCUMENTS

| | | |
|---|---|---|
| 2016/0067031 A1 | 3/2016 | Kassab et al. |
| 2016/0081799 A1 | 3/2016 | Leo et al. |
| 2016/0095703 A1 | 4/2016 | Thomas et al. |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324639 A1 | 11/2016 | Nguyen et al. |
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor et al. |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056166 A1 | 3/2017 | Ratz et al. |
| 2017/0056171 A1 | 3/2017 | Cooper et al. |
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100246 A1 | 4/2017 | Rust et al. |
| 2017/0112620 A1 | 4/2017 | Curley et al. |
| 2017/0128208 A1 | 5/2017 | Christianson et al. |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0172738 A1* | 6/2017 | Kassas ............... A61F 2/2418 |
| 2017/0181851 A1 | 6/2017 | Annest |
| 2017/0181852 A1* | 6/2017 | Kassas ............... A61F 2/2433 |
| 2017/0189177 A1 | 7/2017 | Schweich, Jr. et al. |
| 2017/0196690 A1 | 7/2017 | Racchini et al. |
| 2017/0209266 A1 | 7/2017 | Lane et al. |
| 2017/0209268 A1 | 7/2017 | Cunningham et al. |
| 2017/0216023 A1 | 8/2017 | Lane et al. |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini et al. |
| 2017/0281337 A1 | 10/2017 | Campbell |
| 2017/0281341 A1 | 10/2017 | Lim et al. |
| 2017/0296340 A1 | 10/2017 | Gross et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson et al. |
| 2017/0348100 A1 | 12/2017 | Lane et al. |
| 2017/0360557 A1 | 12/2017 | Kheradvar et al. |
| 2017/0360558 A1* | 12/2017 | Ma ..................... A61F 2/2409 |
| 2017/0360561 A1 | 12/2017 | Bell et al. |
| 2018/0014932 A1 | 1/2018 | Hammer et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0099124 A1 | 4/2018 | McLoughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193140 A1 | 7/2018 | Vidlund |
| 2018/0200049 A1* | 7/2018 | Chambers ............. A61F 2/2436 |
| 2018/0206983 A1* | 7/2018 | Noe ..................... A61F 2/2445 |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1 | 9/2018 | Zhang et al. |
| 2018/0256327 A1 | 9/2018 | Perszyk et al. |
| 2018/0256329 A1* | 9/2018 | Chambers ............. A61F 2/2412 |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung et al. |
| 2018/0289485 A1 | 10/2018 | Rajagopal et al. |
| 2018/0296325 A1 | 10/2018 | McLean |
| 2018/0296335 A1 | 10/2018 | Miyashiro |
| 2018/0296337 A1 | 10/2018 | Duhay et al. |
| 2018/0296341 A1* | 10/2018 | Noe ..................... A61F 2/2412 |
| 2018/0303488 A1 | 10/2018 | Hill |
| 2018/0303612 A1 | 10/2018 | Pasquino et al. |
| 2018/0311037 A1 | 11/2018 | Morriss et al. |
| 2018/0311474 A1 | 11/2018 | Tyler, II et al. |
| 2018/0318073 A1 | 11/2018 | Tseng et al. |
| 2018/0318078 A1 | 11/2018 | Willard |
| 2018/0325665 A1 | 11/2018 | Gurovich et al. |

(56) References Cited

U.S. PATENT DOCUMENTS

| | | |
|---|---|---|
| 2018/0325671 A1 | 11/2018 | Abunassar et al. |
| 2018/0333259 A1 | 11/2018 | Dibie |
| 2018/0338832 A1 | 11/2018 | Ganesan et al. |
| 2018/0344456 A1 | 12/2018 | Barash et al. |
| 2018/0353293 A1* | 12/2018 | Colavito ............... A61F 2/2412 |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008636 A1 | 1/2019 | Francis et al. |
| 2019/0008640 A1 | 1/2019 | Cooper et al. |
| 2019/0015188 A1 | 1/2019 | Eigler et al. |
| 2019/0021834 A1 | 1/2019 | Nir et al. |
| 2019/0029819 A1* | 1/2019 | Huber ................. A61B 17/3421 |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0069995 A1 | 3/2019 | Levi et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler et al. |
| 2019/0262129 A1* | 8/2019 | Cooper ................. A61F 2/2409 |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0365538 A1* | 12/2019 | Chambers ............ A61F 2/2454 |
| 2019/0388219 A1 | 12/2019 | Lane et al. |
| 2020/0121452 A1 | 4/2020 | Saikrishnan et al. |
| 2020/0121458 A1* | 4/2020 | Vidlund ............... A61F 2/2436 |
| 2020/0179146 A1* | 6/2020 | Christianson ......... A61F 2/2436 |
| 2020/0188097 A1* | 6/2020 | Perrin .................. A61F 2/2409 |
| 2020/0237506 A1* | 7/2020 | Christianson .......... B33Y 80/00 |
| 2020/0289259 A1 | 9/2020 | Christianson et al. |
| 2020/0289263 A1* | 9/2020 | Christianson ......... A61F 2/2436 |
| 2021/0000592 A1* | 1/2021 | Christianson ......... A61F 2/2418 |
| 2021/0137677 A1* | 5/2021 | Christianson ......... A61F 2/2436 |
| 2021/0154011 A1 | 5/2021 | Christianson et al. |
| 2021/0186693 A1* | 6/2021 | Vidlund, I ............. A61F 2/243 |
| 2021/0220126 A1* | 7/2021 | Perrin .................. A61F 2/2418 |
| 2021/0220127 A1 | 7/2021 | Vidlund et al. |
| 2021/0220134 A1* | 7/2021 | Christianson ......... A61F 2/2418 |
| 2021/0228349 A1 | 7/2021 | Vidlund et al. |
| 2021/0236280 A1* | 8/2021 | Christianson ......... A61F 2/2418 |
| 2021/0244533 A1 | 8/2021 | Vidlund et al. |
| 2021/0244535 A1 | 8/2021 | Iyer et al. |
| 2021/0244536 A1* | 8/2021 | Christianson ......... A61F 2/2439 |
| 2021/0290381 A1* | 9/2021 | Vidlund ............... A61F 2/2418 |
| 2021/0290385 A1 | 9/2021 | Christianson et al. |
| 2021/0330459 A1 | 10/2021 | Christianson et al. |
| 2021/0353412 A1 | 11/2021 | Christianson et al. |
| 2022/0000614 A1 | 1/2022 | Vidlund et al. |

FOREIGN PATENT DOCUMENTS

| | | |
|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |

(56) References Cited

FOREIGN PATENT DOCUMENTS

| | | |
|---|---|---|
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | 103153232 B | 9/2016 |
| CN | 106061437 A | 10/2016 |
| CN | 106068109 A | 11/2016 |
| CN | 106073946 A | 11/2016 |
| CN | 106255475 A | 12/2016 |
| CN | 103917194 B | 2/2017 |
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |
| CN | 106890035 A | 6/2017 |
| CN | 106943207 A | 7/2017 |
| CN | 106999054 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | 1301225 A2 | 4/2003 |
| EP | 1684666 A2 | 8/2006 |
| EP | 1996246 A2 | 12/2008 |
| EP | 2211779 A1 | 8/2010 |
| EP | 2254513 A1 | 12/2010 |
| EP | 2263605 A1 | 12/2010 |
| EP | 2273947 A1 | 1/2011 |
| EP | 2296744 A1 | 3/2011 |
| EP | 2379008 A2 | 10/2011 |
| EP | 2400926 A2 | 1/2012 |
| EP | 2427145 A2 | 3/2012 |
| EP | 1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 B1 | 4/2015 |
| EP | 2444031 B1 | 7/2015 |
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |
| EP | 3062745 A1 | 9/2016 |
| EP | 3071149 A1 | 9/2016 |
| EP | 2282700 B1 | 11/2016 |
| EP | 2967854 B1 | 11/2016 |
| EP | 1998713 B1 | 12/2016 |
| EP | 3099271 A1 | 12/2016 |

(56) References Cited

FOREIGN PATENT DOCUMENTS

| | | |
|---|---|---|
| EP | 3100701 A1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | 3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | 2560580 B1 | 6/2019 |
| EP | 3508113 A1 | 7/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3552584 A1 | 10/2019 |
| EP | 3552655 A1 | 10/2019 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008091925 A2 | 7/2008 |

(56) References Cited

FOREIGN PATENT DOCUMENTS

| | | |
|---|---|---|
| WO | WO-2008103280 A2 | 8/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2010119110 A1 | 10/2010 |
| WO | WO-2011112706 A2 | 9/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |
| WO | WO-2014137805 A1 | 9/2014 |
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017136596 A1 | 8/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |

(56) References Cited

FOREIGN PATENT DOCUMENTS

| WO | WO-2019126518 A1 | 6/2019 |
|---|---|---|
| WO | WO-2019131148 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO 2019/195860 | 10/2019 |
| WO | WO-2019190800 A1 | 10/2019 |
| WO | WO-2019191102 A1 | 10/2019 |

OTHER PUBLICATIONS

Office Action for U.S. Appl. No. 17/167,983, dated Apr. 13, 2021, 20 pages.
Office Action for U.S. Appl. No. 17/154,438, dated May 3, 2021, 16 pages.
Office Action for U.S. Appl. No. 17/193,936, dated May 27, 2021, 6 pages.
Office Action for U.S. Appl. No. 16/449,420, dated Sep. 1, 2021, 16 pages.
Office Action for U.S. Appl. No. 17/154,227, dated Jun. 18, 2021, 8 pages.
Office Action for U.S. Appl. No. 17/221,547, dated Aug. 4, 2021, 11 pages.
Office Action for U.S. Appl. No. 17/222,182, dated Sep. 2, 2021, 23 pages.
Office Action for U.S. Appl. No. 17/236,219, dated Aug. 4, 2021, 17 pages.
Office Action for U.S. Appl. No. 16/443,862, dated Nov. 12, 2021, 9 pages.
Office Action for U.S. Appl. No. 17/167,988, dated Sep. 22, 2021, 19 pages.
Office Action for U.S. Appl. No. 17/221,547, dated Oct. 21, 2021, 9 pages.
Office Action for U.S. Appl. No. 16/435,687, dated Aug. 7, 2019, 19 pages.
International Search Report and Written Opinion for International Application No. PCT/US2019/051615, dated Mar. 2, 2020, 14 pages.
International Search Report and Written Opinion for International Application No. PCT/US2019/051957, dated Apr. 30, 2020, 16 pages.
Office Action for U.S. Appl. No. 16/155,890, dated Feb. 8, 2019, 13 pages.
Office Action for U.S. Appl. No. 16/448,108, dated Jan. 21, 2020, 14 pages.
Office Action for U.S. Appl. No. 16/448,108, dated Sep. 1, 2020, 14 pages.
Office Action for U.S. Appl. No. 16/455,417, dated Sep. 23, 2019, 11 pages.
International Search Report and Written Opinion for International Application No. PCT/US2019/067010, dated Mar. 10, 2020, 17 pages.
Office Action for U.S. Appl. No. 16/455,740, dated Jul. 24, 2020, 7 pages.
International Search Report and Written Opinion for International Application No. PCT/US2020/015231, dated Apr. 23, 2020, 10 pages.
International Search Report and Written Opinion for International Application No. PCT/US2020/021300, dated Oct. 7, 2020, 6 pages.
International Search Report and Written Opinion for International Application No. PCT/US2020/031390, dated Aug. 3, 2020, 10 pages.
International Search Report and Written Opinion for International Application No. PCT/US2020/013240, dated Jun. 3, 2020, 7 pages.
International Search Report and Written Opinion for International Application No. PCT/US2020/022828, dated May 19, 2020, 12 pages.
Office Action for U.S. Appl. No. 16/442,504, dated Jan. 14, 2020, 11 pages.
International Search Report and Written Opinion for International Application No. PCT/US2020/045195, dated Jan. 8, 2021, 18 pages.
International Search Report and Written Opinion for International Application No. PCT/US2020/047162, dated Dec. 30, 2020, 9 pages.
Office Action for U.S. Appl. No. 16/445,210, dated Jan. 28, 2021, 7 pages.
Office Action for U.S. Appl. No. 16/448,108, dated Mar. 8, 2021, 8 pages.
Office Action for U.S. Appl. No. 16/163,577, dated Mar. 8, 2021, 10 pages.
Office Action for U.S. Appl. No. 17/154,227, dated Mar. 29, 2021, 6 pages.
International Search Report and Written Opinion for International Application No. PCT/US2021/013570, dated Apr. 1, 2021, 9 pages.
Office Action for U.S. Appl. No. 16/711,415, dated Jan. 18, 2022, 7 pages.
Office Action for U.S. Appl. No. 17/388,983, dated Jan. 6, 2022, 11 pages.

\* cited by examiner

FIG. 3
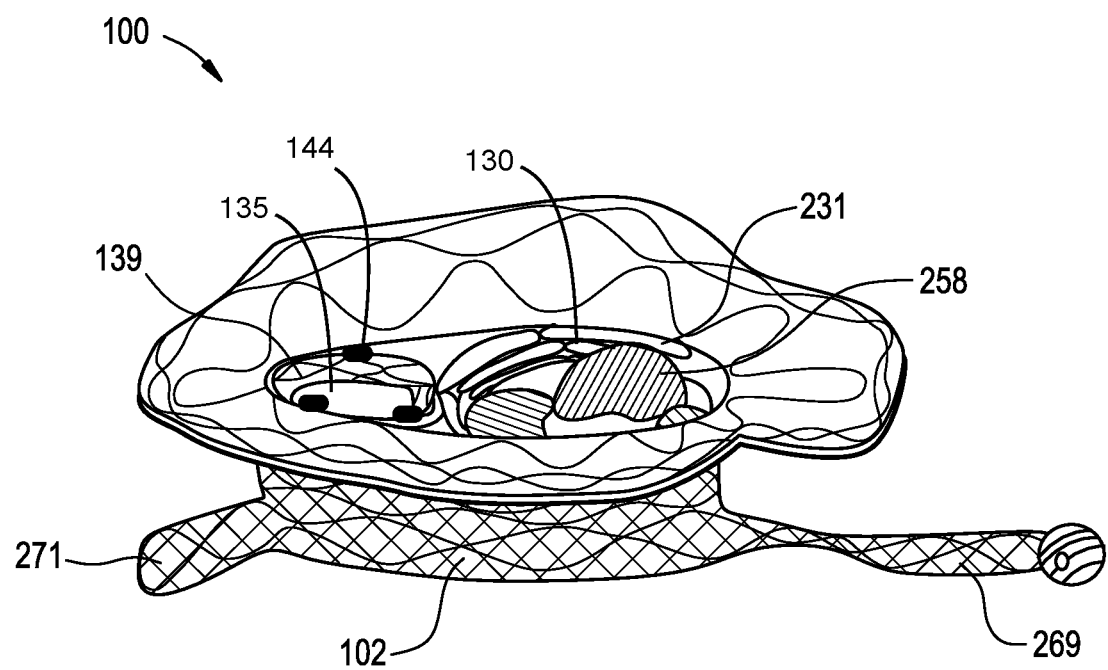
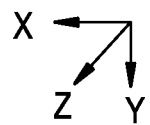

FIG. 35A  modify drum prior to loading

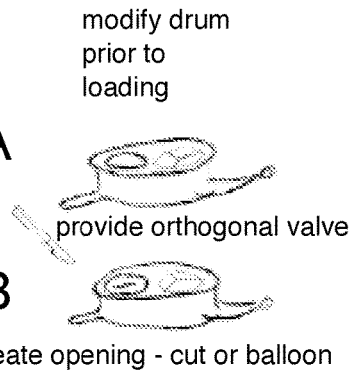

FIG. 35B  provide orthogonal valve

FIG. 35C  create opening - cut or balloon

FIG. 35D  fold valve flat

FIG. 35E  compress valve load valve orthogonally into delivery catheter modify drum after deployment

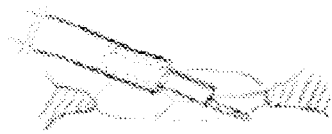

FIG. 36A  deploy valve orthogonally

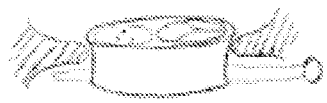

FIG. 36B  locate radio-opaque markers

FIG. 36C  create opening - cut or balloon

FIG. 37 grade of regurgitation

 0.5  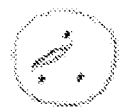 1.0  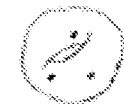 1.5  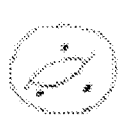 2.0

FIG. 38 sizing stent tube, by intended grade

 0.5   1.0   1.5   2.0

FIG. 49

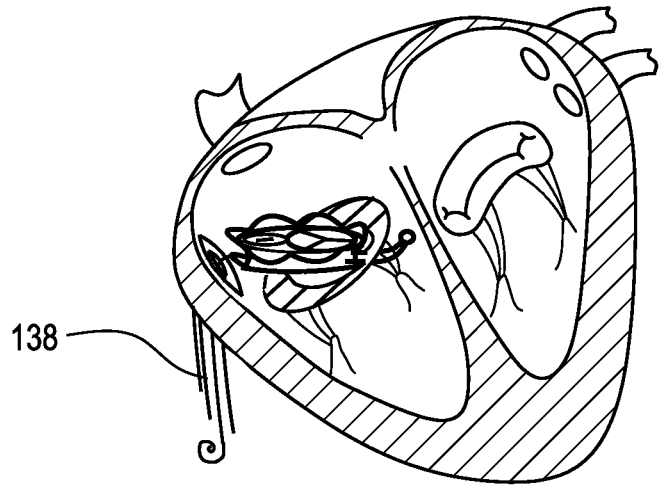

Orthogonal Delivery steps:
1. provide a foldable, compressible prosthetic tricuspid valve
2. load the valve sideways into a delivery catheter
3. advance the valve to the heart via the IVC or the SVC over a pre-placed guidewire that is threaded onto a subannular distal tab
4. partially expel the valve to position the distal subannular tab and to allow the valve leaflets to begin functioning
5. complete deployment of the valve into the native annulus
— —
6. optionally: if the regurg drum was not opened prior to loading into the delivery catheter, a cutting tool or balloon tool can be advanced and a 1-2mm opening is made in the tissue covering of the drum frame
— —
7. optionally: a pacemaker wire set can be advanced through the opening in the regurg drum and the pacemaker wire(s) attached at or near the target nodes

TRICUSPID REGURGITATION CONTROL DEVICES FOR ORTHOGONAL TRANSCATHETER HEART VALVE PROSTHESIS

CROSS-REFERENCE TO RELATED APPLICATIONS

This application is a continuation of International Patent Application Serial No. PCT/US2020/021300, filed Mar. 5, 2020, entitled "Tricuspid Regurgitation Control Devices for Orthogonal Transcatheter Heart Valve Prosthesis," which claims priority to and the benefit of U.S. Provisional Patent Application Ser. No. 62/813,770, filed Mar. 5, 2019, entitled "Tricuspid Regurgitation Control Devices for Orthogonal Transcatheter Heart Valve Prosthesis," the disclosure of each of which is incorporated herein by reference in its entirety.

BACKGROUND OF THE INVENTION

Field of the Invention

The invention relates to an access and occluder device, and in particular a heart valve regurgitation drum and optional closure disk and/or tubular stent to manage and provide levels of intentional regurgitation within a transcatheter heart valve replacement (A61F2/2412).

Description of the Related Art

In 1952 surgeons implanted the first mechanical heart valve, a ball valve that could only be placed in the descending aorta instead of the heart itself. For this reason, it did not fully correct the valve problem, only alleviate the symptoms. However, it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting die technology allowed blood to flow in a more natural way while reducing damage to blood cells from mechanical forces. However, the struts of these valves tended to fracture from fatigue over time. As of 2003, more than 100,000 Omniscience and 300,000 Hall-Kaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement.

Additionally, a problem with stent-style replacement valves is that they often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

The present invention is directed to an access and occluder device, and in particular a heart valve regurgitation drum and optional closure component and/or a perforated tubular stent to manage and provide levels of intentional regurgitation within a transcatheter heart valve replacement, and in particular, within an orthogonally (length-wise, along z-axis) delivered transcatheter prosthetic heart valve.

In a preferred embodiment, a heart valve regurgitation drum with an optional closure component and/or tubular stent for an orthogonally delivered transcatheter prosthetic heart valve comprises a first inner flow control component/valve, a second inner regurgitation control component, and an outer annular support frame having compressible wire cells that facilitate folding flat along the z-axis and compressing the valve vertically along the y-axis, or orthogonally to the central axis of the flow control component, allowing a very large diameter valve to be delivered and deployed to the tricuspid valve from the inferior vena cava or superior vena cava, or trans-septally (transatrially, across fossa ovalis or adjacent tissue) to the mitral valve, the valve having a height of about 5-60 mm and a diameter of about 25-80 mm, without requiring an oversized diameter catheter and without requiring delivery and deployment from a catheter at an acute angle of approach.

In another preferred embodiment, the invention provides device to manage and provide grades of intentional regurgitation within an orthogonally delivered transcatheter prosthetic heart valve, comprising: an orthogonally delivered transcatheter prosthetic heart valve having (i) a first inner flow control component, (ii) a second inner regurgitation control component, and (iii) an outer annular support frame, the second inner regurgitation control component having a foldable and compressible frame, a tissue cover attached to the frame, and an flow modifier mounted within a reinforcement ring mounted on the tissue cover, the flow modifier selected from a occluder, a tubular stent, and a tubular stent having an occluder within a lumen of the tubular stent, said tissue cover having one or more radio-opaque markers, and said second inner regurgitation control component mounted within the outer support frame of the prosthetic heart valve, the self-expanding annular outer support frame having a central channel, an outer perimeter wall circumscribing a central vertical axis in an expanded configuration, an atrial collar mounted along a top edge of the perimeter wall, a distal anchoring tab mounted on a distal side of the outer annular support frame, and a proximal anchoring tab mounted on a proximal side of the outer annular support frame, the first inner flow control component mounted within the outer annular support frame adjacent to the second inner regurgitation control component, said first inner flow control component configured to permit blood flow in a first direction through an inflow end of the valve and block blood flow in a second direction, opposite the first direction, through an outflow end of the valve, the first inner flow control component having leaflet frame with 2-4 flexible leaflets mounted thereon, wherein each of said foldable and compressible frame of the second inner regurgitation control component, said leaflet frame of the first inner flow control component, and said outer support frame are each foldable along a horizontal z-axis from a cylindrical configuration to a flattened cylinder configuration and compressible along a vertical y-axis to a shortened configuration, wherein the prosthetic heart valve is compressible to a compressed configuration for introduction into the body using a delivery catheter for implanting at a desired location in the body, said compressed configuration is oriented along a horizontal x-axis that is substantially parallel to a lengthwise cylindrical axis of the delivery catheter, said horizontal x-axis oriented at an intersecting angle of between 45-135 degrees to the central vertical y-axis, and expandable to an expanded configuration having the horizontal x-axis at an intersecting angle of between 45-135 degrees to the central vertical y-axis, wherein the valve has a height of about 5-60 mm and a diameter of about 25-80 mm.

In another preferred embodiment, the invention provides a valve wherein the annular outer support frame has an inner surface and an outer surface, said inner surface and said outer surface covered with a biocompatible material selected from the following consisting of: the inner surface covered with pericardial tissue, the outer surface covered with a woven synthetic polyester material, and both the inner surface covered with pericardial tissue and the outer surface covered with a woven synthetic polyester material.

In another preferred embodiment, the invention provides a valve wherein the distal anchoring tab, the proximal anchoring tab, or both, are comprised of wire loop, a wire frame, a laser cut frame, an integrated frame section, or a stent, and extend from about 10-40 mm away from the side of the annular outer support frame.

In another preferred embodiment, the invention provides a valve further comprising an upper distal anchoring tab attached to a distal upper edge of the annular support frame, the upper distal anchoring tab comprised of wire loop, a wire frame, a laser cut frame, an integrated frame section, or a stent, and extends from about 2-20 mm away from the annular outer support frame.

In another preferred embodiment, the invention provides a valve comprising at least one tissue anchor connected to the annular outer support frame for engaging native tissue.

In another preferred embodiment, the invention provides a valve wherein the annular outer support frame is comprised of compressible wire cells selected from the group consisting of: braided-wire cells, laser-cut wire cells, photolithography produced wire cells, 3D printed wire cells, wire cells formed from intermittently connected single strand wires in a wave shape, a zig-zag shape, or spiral shape, and combinations thereof.

In another preferred embodiment, the invention provides a valve wherein the annular outer support frame is covered on an outer surface with a pericardium tissue, a polyester material or similar biocompatible material.

In another preferred embodiment, the invention provides a method of providing intentional regurgitation in an implanted transcatheter prosthetic heart valve, comprising the steps: cutting or perforating a section of the tissue cover within the reinforcement ring of the second inner regurgitation control component of claim 1 to form an aperture by deploying a catheter cutting tool to the implanted valve of claim 1, where the valve of claim 1 is implanted as a prosthetic heart valve in a patient.

In another preferred embodiment, the invention provides a method, comprising an additional step of deploying into the aperture a flow modifier selected from an occluder, a tubular stent, and a tubular stent having an occluder within a lumen of the tubular stent.

In another preferred embodiment, the invention provides a method of controlling or modifying regurgitation in a patient having an orthogonally delivered transcatheter prosthetic heart valve, comprising the steps: Step 1. providing a foldable, compressible prosthetic tricuspid valve according to claim 1; Step 2. loading the valve sideways into a delivery catheter; Step 3. advancing the valve to a tricuspid valve of a heart of the patient via an inferior vena cava (IVC) or superior vena cava (SVC) over a pre-placed guidewire that is threaded onto a subannular distal tab; Step 4. partially expelling the valve to position the distal subannular tab and to allow valve leaflets to begin functioning; Step 5. completing deployment of the valve into the native annulus; and Step 6. advancing a cutting tool or balloon tool through the delivery catheter to the deployed valve and creating a 1-5 mm opening in the tissue covering of the inner regurgitation control component.

In another preferred embodiment, the invention provides a method of controlling or modifying regurgitation, further comprising: Step 7. advancing a pacemaker wire set through the opening in the in the tissue covering of the inner regurgitation control component and attaching the pacemaker wire(s) at or near the target conduction nodes.

BRIEF DESCRIPTION OF THE SEVERAL VIEWS OF DRAWING

FIG. 1 is an illustration of a side perspective view of an inner regurgitation control component with radio-opaque markers as part of an orthogonally deliverable transcatheter heart valve with a collapsible flow control component mounted within the annular outer support frame, the collapsible (inner) flow control component having leaflet frame with 2-4 flexible leaflets mounted thereon, the leaflet frame foldable along a z-axis from a cylindrical configuration to a flattened cylinder configuration and compressible along a vertical axis (y-axis) to a shortened configuration, and the valve having a superelastic wire loop distal tab and a superelastic wire loop proximal tab according to the invention.

FIG. 2 is an illustration of a side perspective exploded view of an embodiment having an inner regurgitation control component with radio-opaque markers, three leaflet cusp or pockets mounted within a foldable and compressible inner wire frame, the inner leaflet frame is mounted within an annular outer support frame ("outer frame") which has a collar component attached circumferentially at a top edge of the outer frame, a dual tab component, and a mesh component, according to the invention.

FIG. 3 is an illustration of a side perspective view of an inner regurgitation control component with radio-opaque markers as part of an orthogonally deliverable transcatheter heart valve with a collapsible flow control component mounted within the annular outer support frame, the collapsible (inner) flow control component having leaflet frame with 2-4 flexible leaflets mounted thereon, the inner leaflet frame foldable along a z-axis from a cylindrical configuration to a flattened cylinder configuration and compressible along a vertical axis (y-axis) to a shortened configuration, and the valve having a superelastic wire loop distal tab and a superelastic wire loop proximal tab according to the invention.

FIG. 4 is an illustration of a side perspective exploded view of an embodiment having an inner regurgitation control component with radio-opaque markers, three leaflet cusp or pockets mounted within a foldable and compressible inner wire frame, the inner leaflet frame is mounted within an outer frame which has a collar component attached circumferentially at a top edge of the outer frame, a pair of integrated, independent tab components, and a mesh component, according to the invention.

Figure 30:
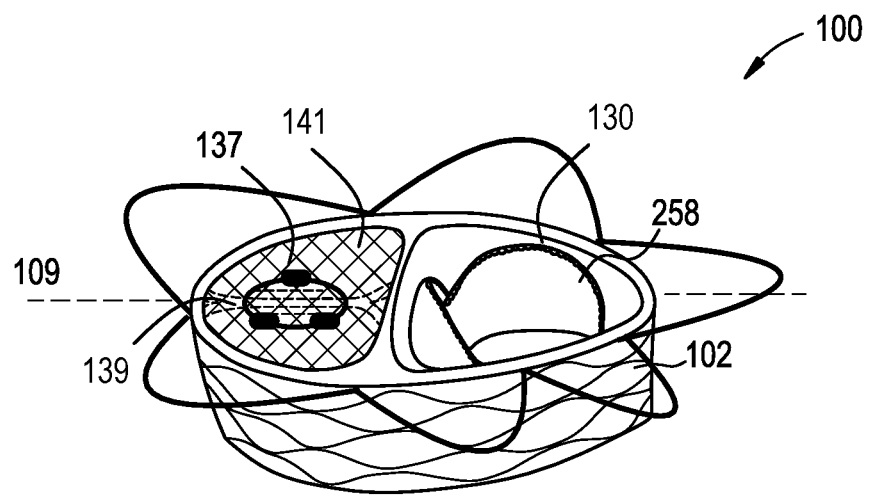

FIG. 30 is an illustration of a top perspective view of an assembled valve with an inner regurgitation control component with radio-opaque markers, and an outer frame, a flow control component having an inner leaflet frame and three leaflet pockets/cusps, an inner spacer frame, and a tissue cover over the spacer frame, fold-line is shown as a dashed line on the tissue cover, according to the invention.

Figure 31:
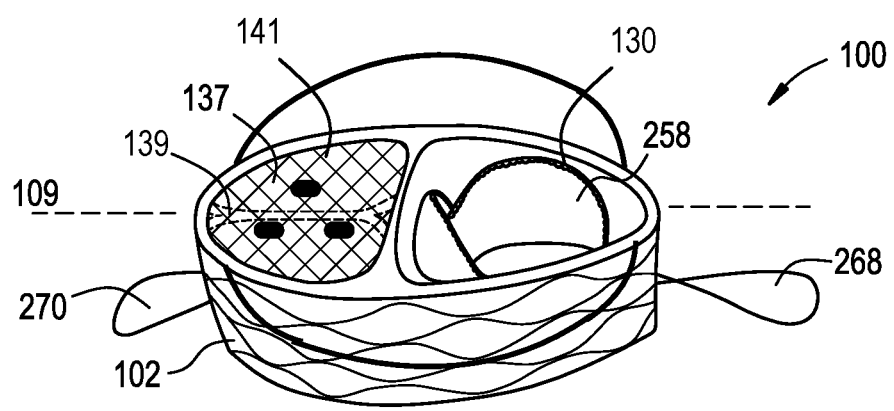

FIG. 31 is an illustration of a top perspective view of an assembled valve with an inner regurgitation control component with radio-opaque markers, and an outer frame, a first sub-annular anchoring/positioning tab mounted on the outer frame adjacent the flow control component, a second sub-annular anchoring/positioning tab mounted on the outer frame in a different location, a flow control component having an inner leaflet frame and three leaflet pockets/cusps, an inner spacer frame, and a tissue cover over the spacer frame, fold-line is shown as a dashed line on the tissue cover, according to the invention.

Figure 32:
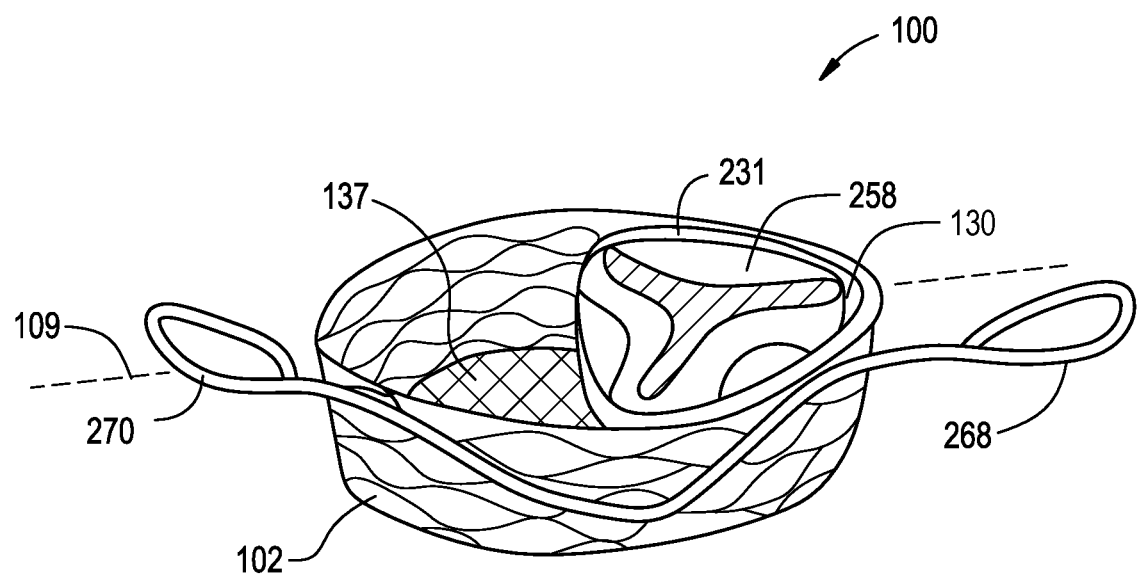

FIG. 32 is an illustration of a bottom perspective view of an assembled valve with an outer frame, a first sub-annular anchoring/positioning tab mounted on the outer frame adjacent the flow control component, a second sub-annular anchoring/positioning tab mounted on the outer frame in a different location, a flow control component having an inner leaflet frame and three leaflet pockets/cusps, an inner spacer frame and a tissue cover over the spacer frame, fold-line is shown as a dashed line on the tissue cover, and hemodynamic washing cavity is shown under the covered inner spacer frame, according to the invention.

Figure 33:
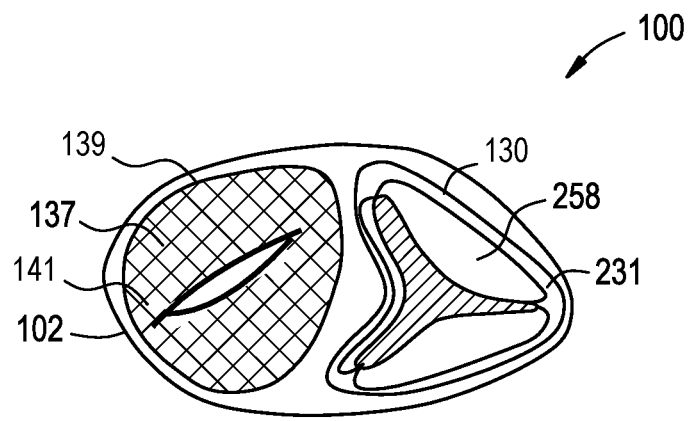

FIG. 33 is an illustration of a top view of an assembled valve with an inner regurgitation control component, and an outer frame, a flow control component having an inner leaflet frame and three leaflet pockets/cusps, an inner spacer frame, and a tissue cover over the spacer frame, according to the invention.

Figure 34:
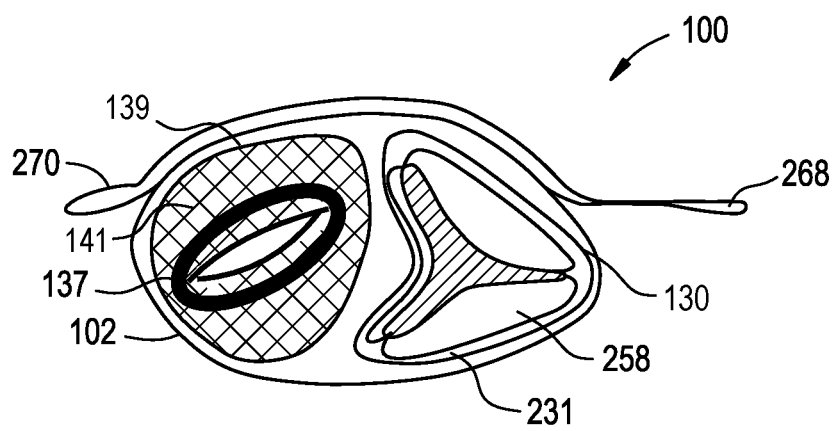

FIG. 34 is an illustration of a top view of an assembled valve with an inner regurgitation control component, and an outer frame, a first sub-annular anchoring/positioning tab mounted on the outer frame adjacent the flow control component, a second sub-annular anchoring/positioning tab mounted on the outer frame in a different location, a flow control component having an inner leaflet frame and three leaflet pockets/cusps, an inner spacer frame, and a tissue cover over the spacer frame, according to the invention.

FIGS. 35A-35E are illustrations of a step by step process where the tissue drum is perforated prior to loading the valve orthogonally into the delivery catheter.

FIGS. 36A-36C are illustrations of a step by step process where the tissue drum is perforated after the valve is expelled orthogonally from the delivery catheter, and deployed into the native annulus.

FIG. 37 is an illustration of how a user can match the size of the aperture to the amount of regurgitation desired, e.g., a range from 0.5-2.0 grades of regurgitation.

FIG. 38 is an illustration of how a user can match the size of the lumen of a tubular stent that can be deployed into the aperture to match the amount of regurgitation desired, e.g., a range from 0.5-2.0 grades of regurgitation.

Figure 39:
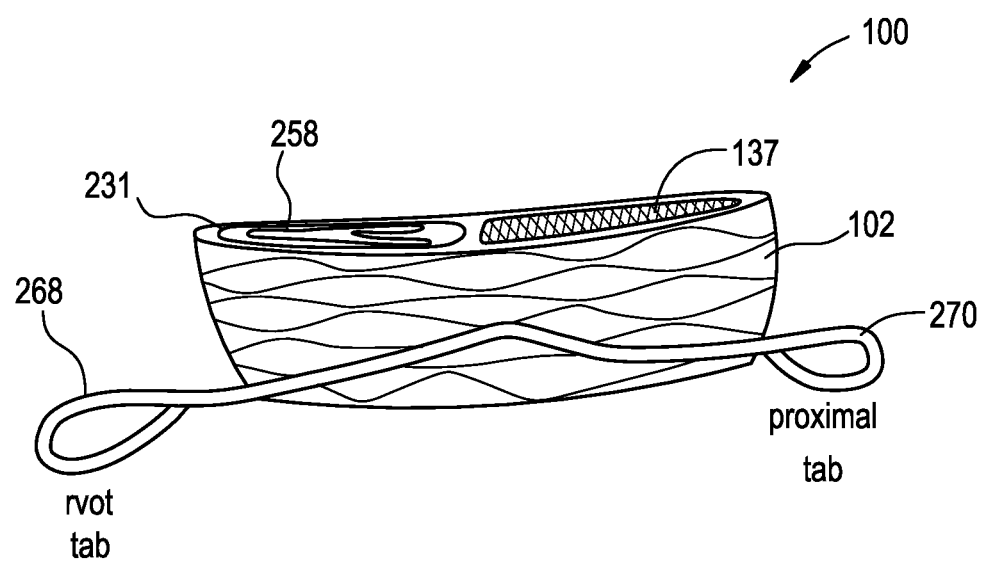

FIG. 39 is an illustration of a side septal plan view of a tabbed valve with sub-annular anchoring and/or positioning tab extending towards the viewer, and second sub-annular tab extending away, and with foldable and compressible wireframe construction visible, according to the invention.

FIGS. 40A-40F are illustrations of a closure device used to close a perforation in an inner regurgitation control component.

Figure 41:
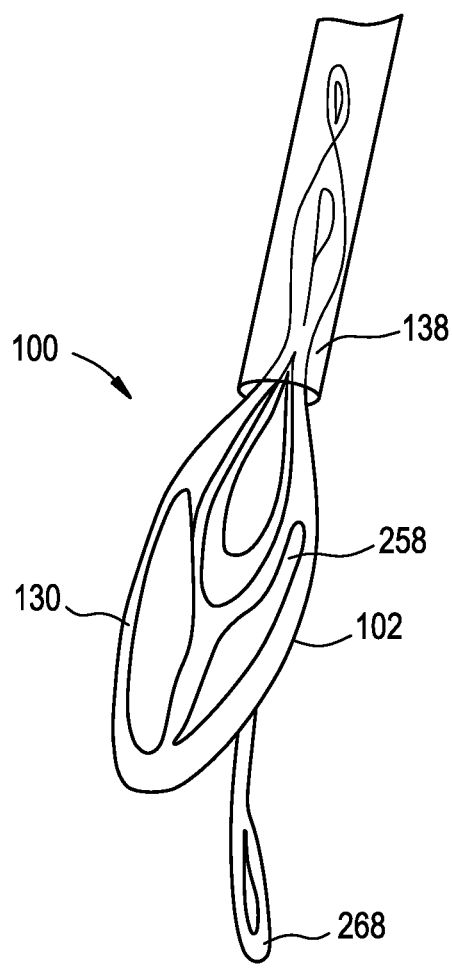

FIG. 41 is an illustration of a top view of a valve partially expelled from a delivery catheter, with a distal tab leading the valve (along guide wire not shown) to the deployment location, with distal flow control component beginning to open and showing two of three leaflets opening from a folded, lie-flat configuration with the third leaflet opening from a folded configuration where it is folded back on itself when in the delivery catheter, according to the invention.

Figure 42:
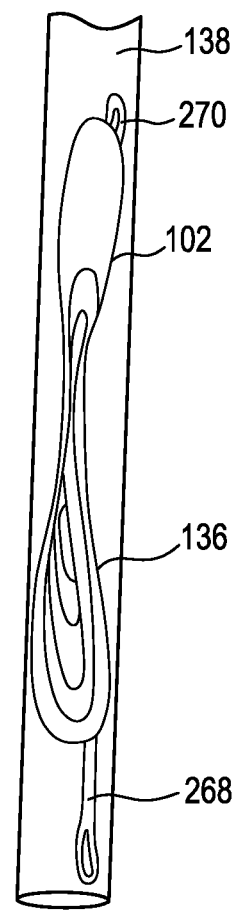

FIG. 42 is an illustration of a top view of a valve compressed (orthogonally loaded) within a delivery catheter with a first tab extending forward along an x-axis and a second trailing tab extending backwards along the x-axis, according to the invention.

Figure 43:
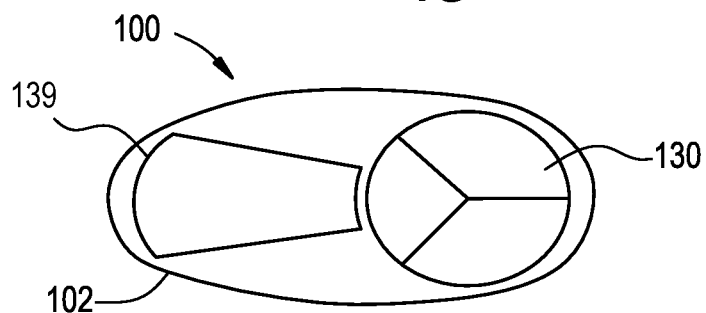

FIG. 43 is an illustration of a top view of a valve having an outer frame, an off-center inner flow control component (leaflet in frame) and an irregularly shaped spacer/support frame, according to the invention.

Figure 44:
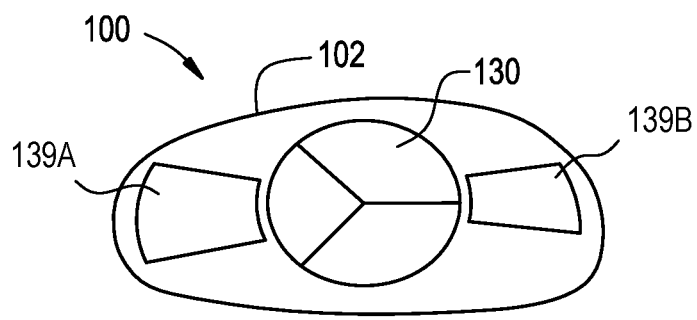

FIG. 44 is an illustration of a top view of a valve having an outer frame, a centrally located inner flow control component (leaflet in frame) and a pair of irregularly shaped spacer/support frames on opposing sides of the inner flow control component, according to the invention.

Figure 45:
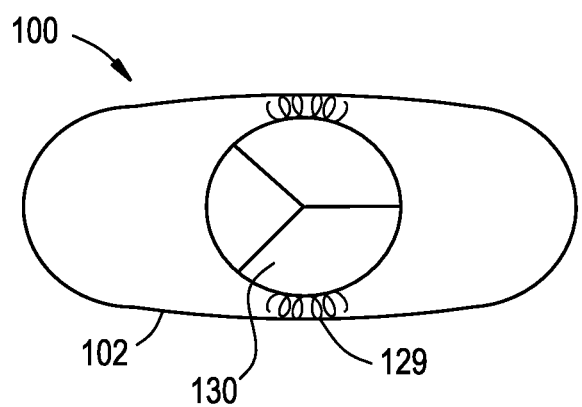

FIG. 45 is an illustration of a top view of a valve having an outer frame, and an inner flow control component (leaflet in frame) and a plurality of sewn attachment points where the inner flow control component is sewn to the outer frame, according to the invention.

Figure 46:
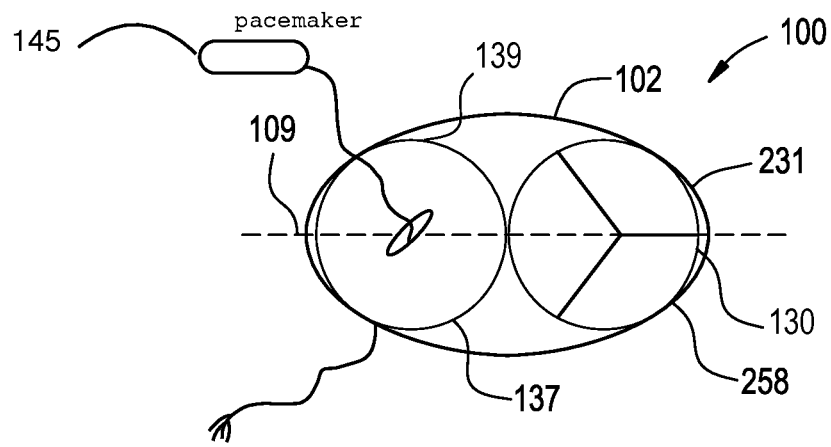

FIG. 46 is an illustration of a top view of a valve having a pacemaker lead wire set mounted within the perforation in an inner regurgitation control component, an outer frame, an off-center inner flow control component, and an inner spacer frame, all three structures foldable along the same x-axis, according to the invention.

Figure 47:
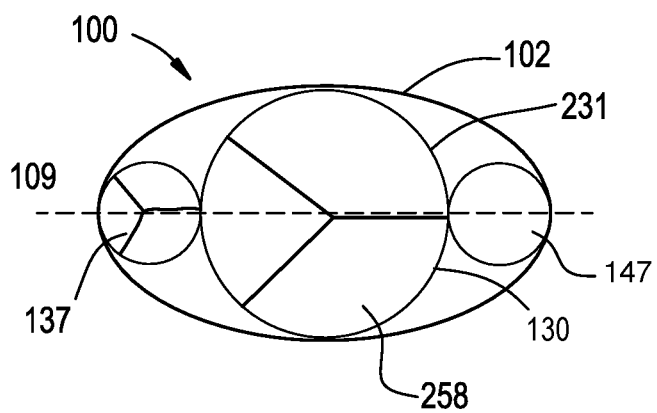

FIG. 47 is an illustration of a top view of a valve having an outer frame, a centrally positioned inner flow control component, and a pair of smaller cylindrical inner spacer frames mounted on opposing sides of the inner flow control component to provide support within the interior dimension of the outer frame, all four structures foldable along the same x-axis, according to the invention.

Figure 48:
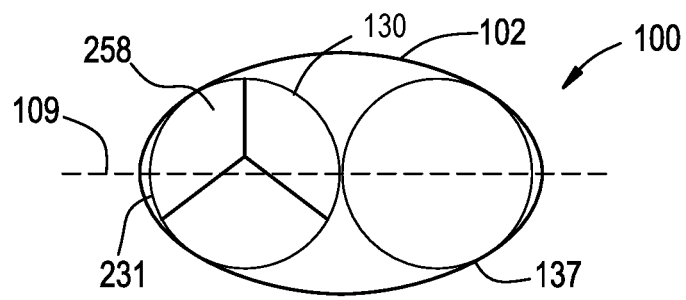

FIG. 48 is an illustration of a top view of a valve having an outer frame, a proximally located off-set inner flow control component, and a distal-side inner spacer frame, all three structures foldable along the same x-axis, according to the invention.

FIG. 49 is an illustration of a side view of a human heart having a trans-femoral/IVC or SVC delivery catheter having expelled an orthogonal prosthetic valve for low-angle of deployment access to the tricuspid valve, according to the invention.

DETAILED DESCRIPTION OF THE INVENTION

The invention is directed to a dual-tab transcatheter heart valve replacement that is a low profile, orthogonally delivered implantable prosthetic heart valve having an ring-shaped or annular support frame, an inner 2- or 3-panel sleeve, an elongated sub-annular distal anchoring tab extending into the right ventricular outflow tract, an elongated sub-annular proximal anchoring tab extending into the proximal sub-annular space, preferably between the anterior and the posterior leaflets.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Orthogonal

In the description and claims herein, the term "orthogonal" is used to describe that the valves of the present invention are compressed and delivered at a roughly 90 degree angle compared to traditional transcatheter heart valves. Traditional valves have a central cylinder axis that is parallel to the length-wise axis of the delivery catheter and are deployed from the end of the delivery catheter in a manner akin to pushing a closed umbrella out of a sleeve. The valves of the present invention are compressed and delivered in a sideways manner. Traditional valves can only be expanded as large as what the internal diameter of the delivery catheter will allow. Efforts to increase the expanded diameter of traditional valves have run into the problems of trying to compress too much material and structure into too little space.

Mathematically, the term orthogonal refers to an intersecting angle of 90 degrees between two lines or planes. As used, herein the term "substantially orthogonal" refers to an intersecting angle ranging from 75 to 105 degrees. The intersecting angle or orthogonal angle refers to both (i) the relationship between the length-wise cylindrical axis of the delivery catheter and the long-axis of the compressed valve of the invention, where the long-axis is perpendicular to the central cylinder axis of traditional valves, and (ii) the relationship between the long-axis of the compressed or expanded valve of the invention and the axis defined by the blood flow through the prosthetic heart valve where the blood is flowing, e.g., from one part of the body or chamber of the heart to another downstream part of the body or chamber of the heart, such as from an atrium to a ventricle through a native annulus.

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid. Transcatheter can be synonymous with transluminal and is functionally related to the term "percutaneous" as it relates to delivery of heart valves.

In preferred embodiments of the invention, the transcatheter approach includes (i) advancing to the tricuspid valve or pulmonary artery of the heart through the inferior vena cava via the femoral vein, (ii) advancing to the tricuspid valve or pulmonary artery of the heart through the superior vena cava via the jugular vein, (iii) advancing to the mitral valve of the heart through a trans-atrial approach, e.g., fossa ovalis or lower, via the IVC-femoral or the SVC jugular approach.

Annular Support Frame

In the description and claims herein, the term "annular support frame" and also "wire frame" or "flange or "collar" refers to a three-dimensional structural component that is seated within a native valve annulus and is used as a mounting element for a leaflet structure, a flow control component, or a flexible reciprocating sleeve or sleeve-valve.

In a preferred embodiment, the annular support frame is a self-expanding annular support frame, having a central channel and an outer perimeter wall circumscribing a central vertical axis in an expanded configuration. The perimeter wall encompasses both the collar and the lower body portions.

The perimeter wall can be further defined as having a front wall portion and a back wall portion, which are connected along a near side (to the IVC) or proximal side to a proximal fold area, and connected along a far or distal side to a distal fold area.

This front wall portion can be further defined as having a front upper collar portion and a front lower body portion, and the back wall portion can be further defined as having a back upper collar portion and a back lower body portion.

The annular support frame has a flow control component mounted within the annular support frame and configured to permit blood flow in a first direction through an inflow end of the valve and block blood flow in a second direction, opposite the first direction, through an outflow end of the valve.

Since the frame is preferably made of superelastic metal or alloy such as Nitinol, the frame is compressible. Preferably, the frame is constructed of a plurality of compressible wire cells having an orientation and cell geometry substantially orthogonal to the central vertical axis to minimize wire cell strain when the annular support frame when configured in a vertical compressed configuration, a rolled compressed configuration, or a folded compressed configuration.

Annular Support Frame Structure

The annular support frame can be a ring, or cylindrical or conical tube, made from a durable, biocompatible structural material such as Nitinol or similar alloy, wherein the annular support frame is formed by manufacturing the structural material as a braided wire frame, a laser-cut wire frame, or a wire loop. The annular support frame is about 5-60 mm in height, has an outer diameter dimension, R, of 30-80 mm, and an inner diameter dimension of 31-79 mm, accounting for the thickness of the wire material itself.

As stated, the annular support frame can have a side-profile of a ring shape, cylinder shape, conical tube shape, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. In one preferred embodiment, the annular support frame used in the prosthetic heart valve deployed in the tricuspid annulus may have a complex shape determined by the anatomical structures where the valve is being mounted. For example, in the tricuspid annulus, the circumference of the tricuspid valve may be a rounded ellipse, the septal wall is known to be substantially vertical, and the tricuspid is known to enlarge in disease states along the anterior-posterior line. Accordingly, a prosthetic heart valve may start in a roughly tubular configuration, and be heat shaped to provide an upper atrial cuff or flange for atrial sealing and a lower trans-annular tubular or cylindrical section having an hourglass cross-section for about 60-80% of the circumference to conform to the native annulus along the posterior and anterior annular segments while remaining substantially vertically flat along 20-40% of the annular circumference to conform to the septal annular segment.

Annular Support Frame Covering

The annular support frame is optionally internally or externally covered, partially or completely, with a biocompatible material such as pericardium. The annular support frame may also be optionally externally covered, partially or completely, with a second biocompatible material such as polyester or Dacron®.

Annular Support Frame Purpose

The annular support frame has a central axial lumen where a prosthetic heart valve or flow-control structure, such as a reciprocating compressible sleeve, is mounted across the diameter of the lumen. The annular support frame is also tensioned against the inner aspect of the native annulus and provides structural patency to a weakened annular ring.

Annular Support Frame Optional Collars

The annular support frame may optionally have a separate atrial collar attached to the upper (atrial) edge of the frame, for deploying on the atrial floor, that is used to direct blood from the atrium into the sleeve and to seal against blood leakage around the annular support frame. The annular support frame may also optionally have a separate ventricular collar attached to the lower (ventricular) edge of the frame, for deploying in the ventricle immediately below the native annulus that is used to prevent regurgitant leakage during systole, to prevent dislodging of the device during systole, to sandwich or compress the native annulus or adjacent tissue against the atrial collar, and optionally to attach to and support the sleeve/conduit.

Annular Support Frame Delivery

The annular support frame may be compressed for transcatheter delivery and may be expandable as a self-expandable shape-memory element or using a transcatheter expansion balloon. Some embodiments may have both an atrial collar and a ventricular collar, whereas other embodiments within the scope of the invention include prosthetic heart valves having either a single atrial collar, a single ventricular collar, or having no additional collar structure.

Frame Material

Preferably, the frame is made from a superelastic metal component, such as laser-cut Nitinol tube, or flat sheet or other similarly functioning material such as braided wire. The material may be used for the frame/stent, for the collar, and/or for anchors. It is contemplated as within the scope of the invention to use other shape memory alloys, as well as polymer composites including composites containing carbon nanotubes, carbon fibers, metal fibers, glass fibers, and polymer fibers. It is contemplated that the frame may be constructed as a braid, wire, or laser cut frame. Laser cut frames are preferably made from Nitinol, but also without limitation made from stainless steel, cobalt chromium, titanium, and other functionally equivalent metals and alloys.

One key aspect of the frame design is that it be compressible and when released have the stated property that it returns to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required mechanical behavior.

Laser Cut

One possible construction of the wire frame envisions the laser cutting of a thin, isodiametric Nitinol tube. The laser cuts form regular cutouts in the thin Nitinol tube. In one preferred embodiment, the Nitinol tube expands to form a three-dimensional structure formed from diamond shaped cells. The structure may also have additional functional elements, e.g., loops, anchors, etc. for attaching accessory components such as biocompatible covers, tissue anchors, releasable deployment and retrieval control guides, knobs, attachments, rigging, and so forth.

Secondarily the tube is thermo-mechanically processed using industry standard Nitinol shape forming methods. The treatment of the wire frame in this manner will form a device that has shape memory properties and will readily revert to the memory shape once deployed.

Braided Wire

Another possible construction of the wire frame envisions utilizing simple braiding techniques using a Nitinol wire and a simple braiding fixture. The wire is wound on the braiding fixture in a pattern until an isodiametric tube is formed. Secondarily, the braided wire frame is placed on a shaping fixture and processed using industry standard Nitinol shape forming methods.

Flow Control Component

In the description and claims herein, the term "flow control component" refers in a non-limiting sense to a leaflet structure having 2-, 3-, 4-leaflets of flexible biocompatible material such a treated or untreated pericardium that is sewn or joined to an inner annular support frame (referred to as an "inner leaflet frame" or "leaflet frame") mounted within an outer annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating."

Regurgitation Drum or Inner Regurgitation Control Component

In the description and claims herein, the term "regurgitation drum" or "inner regurgitation control component" refers to a second inner annular support frame mounted within the outer annular support frame next to the first inner annular support frame. The "regurgitation drum" or "inner regurgitation control component" has a foldable and compressible frame, a tissue cover attached to the frame, and a flow modifier mounted within a reinforcement ring mounted on the tissue cover, the flow modifier selected from a channel, an occluder, a tubular stent, and a tubular stent having an occluder within a lumen of the tubular stent, said tissue cover having one or more radio-opaque markers. This "regurgitation drum" or "inner regurgitation control component" can be pre-perforated before the valve is loaded into the delivery catheter, it can be perforated using a catheter tool after the valve has been deployed into the native annulus, the perforation can be reinforced using a stent tube, and the perforation or stent tube can be sealed off using a closure device such as a polyester disk, a nitinol disk, a nitinol disk having a polyester cover, a double-disk (button on each side) closure device, or functionally similar device similar to the devices used to treat patent foramen ovale but modified for use in accessing and closing a, e.g., 1-2 mm perforation in, a regurgitation drum.

Reinforcement Ring

The term reinforcement ring refers to a ring of material such as pericardium, polymer, or biocompatible material, that is mounted on the top surface of the tissue cover of the "regurgitation drum" or "inner regurgitation control component." In a preferred embodiment, the reinforcement ring circumscribes the target area for the perforation and prevent the perforation from tearing or losing patency. In another preferred embodiment, the radio-opaque markers, that are used to guide the catheter cutting/balloon tool, may be mounted on top of or within the reinforcement ring.

Radio-Opaque Marker

The term "radio-opaque marker" refers to a material that allows visibility during fluoroscopy or other radiologic imaging. Examples of radio-opaque marker materials include nitinol, gold, platinum, and combinations or mixtures thereof. Radio-opaque materials may also include powdered or particulate metals that are encompassed within a polymer, glass, or ceramic matrix. The invention contemplates the use of one or more markers, e.g., from 1-10, or from 3-5 markers. The invention contemplates the use of markers mounted in a specific pattern or orientation to provide not only targeting of a perforation location, but also positioning information for the valve itself. For example, use of a three marker pattern provides a central targeting area, but can also provide information on whether the valve is oriented correctly, such as having the septal-collar portion of the prosthetic valve aligned with the septal side of the tricuspid valve.

Tissue Anchor

In the description and claims herein, the term "tissue anchor" or "plication tissue anchor" or "secondary tissue anchor" or "dart" or "pin" refers to a fastening device that connects the upper atrial frame to the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK, that may be mounted on a spoked frame and that runs axially, or down the center of, or within a sewn seam of, the flexible sleeve. The sleeve may be unattached to the support post, or the sleeve may be directly or indirectly attached to the support post.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

Displacement—The volume of fluid displaced by one complete stroke or revolution.

Ejection fraction is a measurement of the percentage of blood leaving your heart each time it contracts. During each heartbeat pumping cycle, the heart contracts and relaxes. When your heart contracts, it ejects blood from the two pumping chambers (ventricles).

As used herein, the terms "proximal" and "distal" are to be taken as relative to a user (e.g., a surgeon or an interventional cardiologist) of the disclosed delivery devices. "Proximal" is to be understood as relatively close to the user and "distal" is to be understood as relatively farther away from the user.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Prosthetic Heart Valve

The term prosthesis or prosthetic encompasses both complete replacement of an anatomical part, e.g., a new mechanical valve replaces a native valve, as well as medical devices that take the place of and/or assist, repair, or improve existing anatomical parts, e.g., native valve is left in place. For mounting within a passive assist cage, the invention contemplates a wide variety of (bio)prosthetic artificial heart valves. Contemplated as within the scope of the invention are ball valves (e.g., Starr-Edwards), bileaflet valves (St. Jude), tilting disc valves (e.g., Bjork-Shiley), stented pericardium heart-valve prosthesis (bovine, porcine, ovine) (Edwards line of bioprostheses, St. Jude prosthetic heart valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Tethers

The tethers are made from surgical-grade materials such as biocompatible polymer suture material. Non-limiting examples of such material include ultra-high-molecular weight polyethylene (UHMWPE), 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines—Anchors—Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium.

In one embodiment, where a prosthetic heart valve may or may not include a ventricular collar, the anchor or dart is not attached to a lower ventricular collar, but is attached directly into annular tissue or other tissue useful for anchoring.

Tube and/or Cover Material—Biological Tissue

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic heart valve for implantation, and U.S. Pat. No. 5,336,616 to LifeCell Corporation discloses acellular collagen-based tissue matrix for transplantation.

Polymers

In one preferred embodiment, the conduit may optionally be made from a synthetic material such a polyurethane or polytetrafluoroethylene.

Where a thin, durable synthetic material is contemplated, e.g., for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes

Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

Covered Wire Frame Materials

Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.l.) using 316 L stainless steel wire frame as base for the drug Tacrolimus and utilizing integrated turbostratic carbofilm as the drug carrier. VESTA sync (MIV Therapeutics) using GenX stainless steel (316 L) as base utilizing microporous hydroxyapatite coating as carrier for the drug Sirolimus. YUKON choice (Translumina) used 316 L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316 L stainless steel coated with polyethylene vinyl acetate (PEVA) and poly-butyl methacrylate (PBMA) for carrying the drug Sirolimus. Taxus (Boston Scientific) utilizes 316 L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying Zotarolimus with phosphorylcholine as drug carrier. BioMatrix employing S-Wire frame (316 L) stainless steel as base with polylactic acid surface for carrying the antiproliferative drug Biolimus. ELIXIR-DES program (Elixir Medical Corp) consisting both polyester and polylactide coated wire frames for carrying the drug Novolimus with cobalt-chromium (Co—Cr) as base. JACTAX (Boston Scientific Corp.) utilized D-lactic polylactic acid (DLPLA) coated (316 L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

EXAMPLES OF PREFERRED EMBODIMENTS INCLUDE THE FOLLOWING DETAILS AND FEATURES

Example—Methods for Delivery

The transcatheter prosthetic heart valve may be percutaneously delivered using a transcatheter process via the femoral through the IVC, carotid, sub-xyphoid, intercostal access across the chest wall, and trans-septal to the mitral annulus through the fossa ovalis.

The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound.

In a preferred embodiment the valve self-expands upon release from the catheter since it is constructed in part from shape-memory material, such as Nitinol®, a nickel-titanium alloy, or a cobalt-chromium alloy, alloys used in biomedical implants.

In another embodiment, the valve may be constructed of materials that requires balloon-expansion after the capsule has been ejected from the catheter into the atrium.

The atrial collar/frame and the flow control component are expanded to their functional diameter, as they are deployed into the native annulus, providing a radial tensioning force to secure the valve. Once the valve is deployed about the tricuspid or mitral annulus, fasteners secure the device about the native annulus. Additional fastening of the device to native structures may be performed, and the deployment is complete. Further adjustments using hemodynamic imaging techniques are contemplated as within the scope of the invention in order to ensure the device is secure, is located and oriented as planned, and is functioning as a substitute or successor to the native tricuspid valve.

Example—Method for Delivery

In another preferred embodiment of the invention, there is provided a method for orthogonal delivery of implantable prosthetic heart valve in the body, the method comprising the steps: (i) advancing a distal end of a guide wire to a distal location, wherein the distal location is a pulmonary artery or a left ventricle of a heart, wherein the guide wire starts outside of a patient using femoral vein access or brachiocephalic vein access, and extends through an inferior vena cava or a superior vena cava to a right atrium, and extends from the right atrium through the tricuspid valve to the pulmonary artery or extends from the right atrium across the atrial septum in a transseptal access through the mitral valve and into a left ventricle; (ii) advancing a delivery catheter over the guide wire to a target location, where the target location is a right atrium of the tricuspid valve or a left atrium of the mitral valve; (iii) advancing and delivering an orthogonally compressed self-expandable prosthetic heart valve to the target location in the body, wherein a compressed configuration of the valve has a long x-axis substantially parallel to a length-wise cylindrical axis of the delivery catheter, wherein the expanded configuration of the valve has a height of about 5-60 mm and a diameter of about 25-80 mm, wherein the valve comprises an annular support frame having a collapsible flow control component mounted within the annular support frame and configured to permit blood flow in a first direction through an inflow end of the valve and block blood flow in a second direction, opposite the first direction, through an outflow end of the valve, the collapsible (inner) flow control component having leaflet frame with 2-4 flexible leaflets mounted thereon, the leaflet frame foldable along a z-axis from a cylindrical configuration to a flattened cylinder configuration and compressible along a vertical axis (y-axis) to a shortened configuration, a distal anchoring tab is mounted on a distal side of the annular support frame, the distal anchoring tab having a length of 10-40 mm and a width of 2-10 mm, wherein the guide wire is threaded through a threading aperture on or within the distal anchoring tab, at least one proximal anchoring tab is mounted on a proximal side of the annular support frame, the proximal anchoring tab having a length of 2-25 mm and a width of 2-10 mm, and a valve advancing tool comprising an elongated sheath wherein the guide wire is within a lumen of the sheath, wherein the outer diameter of the sheath is larger than the inner diameter of the threading aperture on the distal anchoring tab, wherein when the sheath is advanced over the guide wire in a distal direction, and a distal end of the sheath contacts a proximal surface of the threading aperture, the valve is advanced distally through the delivery catheter by the distally-directed pulling force that the sheath imparts to the distal anchoring tab; (iv) partially releasing the valve from the delivery catheter by advancing the sheath over the guide wire, and positioning the distal anchoring tab at a desired anchoring area of the target location, wherein the desired anchoring area is selected from a right ventricular outflow tract (RVOT) of a right ventricle, and a sub-annular area below an $A_1$-$P_1$ antero-lateral commissure of a mitral valve, wherein positioning the distal anchoring tab holds the valve at a raised angle of at least 30 degrees to a localized annular plane relative to the horizontal axis of the valve and the delivery catheter, wherein partially releasing the valve permits blood to flow partially around the prosthetic valve and through the native leaflets, and partially through the flow control component of the prosthetic valve to provide a gradual blood flow transition from flow through native leaflets to complete flow through the prosthetic valve; (v) completing release of the entire valve from the delivery catheter by advancing the sheath over the guide wire, seating the valve in the native annulus by applying a downward force in the direction of the ventricle; and (vi) seating the at least one proximal anchoring tab at a second desired anchoring area.

Example—Method for Delivery

In another preferred embodiment of the invention, there is provided a method for orthogonal delivery of implantable prosthetic heart valve to a desired location in the body, including the tricuspid valve locations, the method comprising the steps: advancing a delivery catheter to the desired location in the body and delivering an expandable prosthetic heart valve to the desired location in the body by releasing the valve from the delivery catheter, wherein the valve comprises an annular support frame having a collapsible flow control component mounted within the annular support frame and configured to permit blood flow in a first direction through an inflow end of the valve and block blood flow in a second direction, opposite the first direction, through an outflow end of the valve, the collapsible (inner) flow control component having leaflet frame with 2-4 flexible leaflets mounted thereon, the leaflet frame foldable along a z-axis from a cylindrical configuration to a flattened cylinder configuration and compressible along a vertical axis (y-axis) to a shortened configuration, a distal anchoring tab mounted on a distal side of the annular support frame, and a proximal anchoring tab mounted on a proximal side of the annular support frame, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the compressed configuration, wherein the valve has a height of about 5-60 mm and a diameter of about 25-80 mm.

Releasing the valve from the delivery catheter is selected from the steps consisting of: (i) pulling the valve out of the delivery catheter using a rigid elongated pushing rod/draw wire that is releasably connected to the distal side of the valve, wherein advancing the pushing rod away from the delivery catheter pulls the compressed valve out of the delivery catheter, or (ii) pushing the valve out of the delivery catheter using a rigid elongated pushing rod that is releasably connected to the proximal side of the valve, wherein advancing the pushing rod out of from the delivery catheter pushes the compressed valve out of the delivery catheter.

The method of delivery may also include the additional step of anchoring one or more tissue anchors attached to the valve into native tissue.

The method of delivery may also include the additional step of positioning the distal anchoring tab of the heart valve prosthesis into the right ventricular outflow tract of the right ventricle.

The method of delivery may also include the additional steps of positioning the distal anchoring tab of the heart valve prosthesis into the right ventricular outflow tract of the right ventricle, and positioning an upper distal anchoring tab into a supra-annular position, and the upper distal anchoring tab providing a supra-annular downward force in the direction of the ventricle and distal anchoring tab providing a sub-annular upward force in the direction of the atrium.

The method of delivery may also include the additional step of rotating the heart valve prosthesis using a steerable catheter along an axis parallel to the plane of the valve annulus.

Example—Method for Loading

In another preferred embodiment of the invention, there is provided a method for orthogonally loading an implantable prosthetic heart valve into a delivery catheter, the method comprising the steps: loading an implantable prosthetic heart valve into a tapering fixture or funnel attached to a delivery catheter, wherein the valve comprises a annular support frame having a flow control component mounted within the annular support frame and configured to permit blood flow in a first direction through an inflow end of the valve and block blood flow in a second direction, opposite the first direction, through an outflow end of the valve, a distal anchoring tab mounted on a distal side of the annular support frame, and a proximal anchoring tab mounted on a proximal side of the annular support frame, wherein said loading is perpendicular or substantially orthogonal to the first direction, wherein the valve is compressible to a compressed configuration for introduction into the body using a delivery catheter for implanting at a desired location in the body, said compressed configuration having a long x-axis oriented at an intersecting angle of between 45-135 degrees to the first direction, and expandable to an expanded configuration having a long x-axis oriented at an intersecting angle of between 45-135 degrees to the first direction, wherein the long x-axis of the compressed configuration of the valve is substantially parallel to a length-wise cylindrical axis of the delivery catheter, wherein the valve has a height of about 5-60 mm and a diameter of about 25-80 mm.

Example—Method for Loading

In another preferred embodiment of the invention, there is provided a method for loading, wherein the step of loading includes attaching a loading accessory to a valve sidewall, to a valve cuff, to the distal anchoring tab, to the proximal anchoring tab, or a combination thereof, wherein the loading accessory is pushing rod or a pulling wire, and wherein the tapering fixture or funnel has a compression element on an inner surface of the tapering fixture or funnel to facilitate compression, iris-ing, or spiraling of the uncompressed valve.

Example—Method for Improving Flow

In another preferred embodiment of the invention, there is provided a method for improving hemodynamic flow during implantation of a transcatheter prosthetic heart valve, comprising: advancing a delivery catheter to the desired location in the body and delivering the valve of claim 1 to the desired location in the body; partially releasing the valve from the delivery catheter to establish blood flow around the partially released valve and establish blood flow through the flow control component; completely releasing the valve from the delivery catheter while maintaining attachment to the valve with a positioning catheter or wire to transition to increased blood flow through the flow control component and decreasing blood flow around the valve; and deploying the valve into a final mounted position to transition to complete blood flow through the flow control component and minimal or no blood flow around the valve, and disconnecting and withdrawing the positioning catheter or wire from the valve.

In another preferred embodiment of the invention, there is provided a method for improving flow, wherein the distal anchoring tab is an RVOT tab positioned in the RVOT during the transition from partial release of the valve to complete release of the valve.

Example—Manufacturing Process

In a preferred embodiment the invention includes a process for manufacturing an orthogonally delivered transcatheter prosthetic heart valve frame, comprising: (i) using additive or subtractive metal or metal-alloy manufacturing to produce a self-expanding annular support frame, wherein the additive metal or metal-alloy manufacturing is 3D printing or direct metal laser sintering (powder melt), and wherein the subtractive metal or metal-alloy manufacturing is photolithography, laser sintering/cutting, CNC machining, electrical discharge machining.

In another preferred embodiment, there is provided a process for manufacturing an orthogonally delivered transcatheter prosthetic heart valve frame, further comprising the steps of: (ii) mounting a flow control component within the valve frame, said flow control component configured to permit blood flow along the central vertical axis through an inflow end of the flow control component and block blood flow through an outflow end of the valve, (iii) covering an outer surface of the valve frame with a pericardium material or similar biocompatible material.

Example—Compression Methods

In another preferred embodiment, there is provided a method of compressing, wherein the implantable prosthetic heart valve is rolled or folded into a compressed configuration using a step selected from the group consisting of: (i) unilaterally rolling into a compressed configuration from one side of the annular support frame; (i) bilaterally rolling into a compressed configuration from two opposing sides of the annular support frame; (iii) flattening the annular support frame into two parallel panels that are substantially parallel to the long-axis, and then rolling the flattened annular support frame into a compressed configuration; and (iv) flattening the annular support frame along a vertical axis to reduce a vertical dimension of the valve from top to bottom.

DRAWINGS

Figure 1:
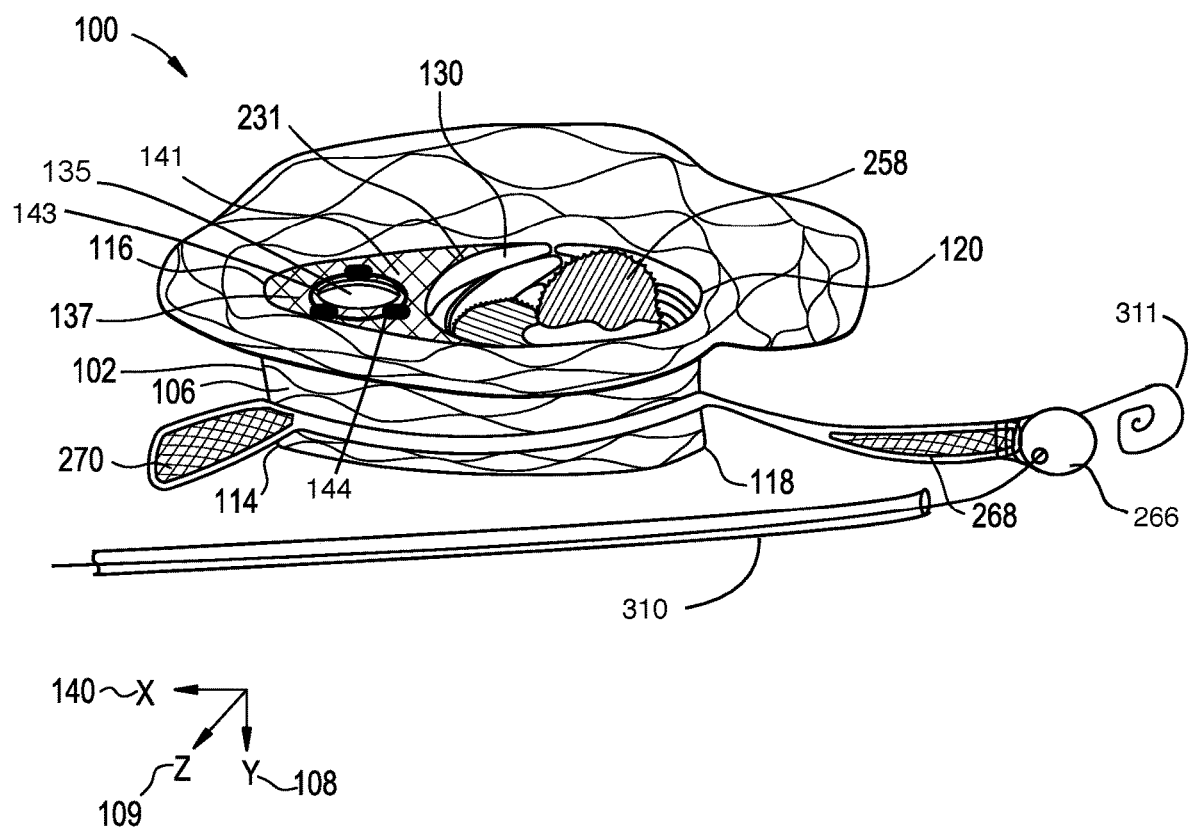

Referring now to the drawings, FIG. 1 is an illustration of a side perspective view of an orthogonally deliverable transcatheter heart valve 100 with inner regurgitation control component 137 mounted within the annular outer support frame 102, a collapsible flow control component 130 mounted within the annular outer support frame 102 (also referred to as "outer frame"), distal tab 268 and proximal tab 270, according to the invention.

The inner regurgitation control component 137 is comprised of tissue cover 141, reinforcement ring 143, radioopaque markers 144, and drum channel 135.

The collapsible (inner) flow control component 130 has an inner leaflet frame 231 (also referred to herein as "leaflet frame") with 2-4 flexible leaflets 258 mounted thereon, the inner leaflet frame 231 foldable along a z-axis 109 from a cylindrical configuration to a flattened cylinder configuration and compressible along a vertical axis 108 (y-axis) to a shortened configuration.

The annular outer support frame 102 is made from a shape-memory material such as Nickel-Titanium alloy, for example NiTiNOL, and is therefore a self-expanding structure starting from a compressed configuration. The annular outer support frame 102 has a central (interior) channel 104 and an outer perimeter wall 106 circumscribing a central vertical axis 108, when in an expanded configuration, and said annular outer support frame 102 having a distal side 118 and a proximal side 114.

The flow control component 130 is mounted within the annular outer support frame 102 and is configured to permit blood flow in a first direction, e.g., atrial to ventricular, through an inflow end of the valve 100 and block blood flow in a second direction, opposite the first direction, through an outflow end of the valve 100.

The inner regurgitation control component 137, like the inner flow control component 130 and the outer frame 102, is foldable and compressible. The inner flow control component 130 comprises leaflet frame 231 with 2-4 flexible leaflets 258 mounted on the leaflet frame 231.

The flow control component 130, and thereby the leaflet frame 231, like the outer frame 102, is foldable along a z-axis (front to back) from a cylindrical configuration to a flattened cylinder configuration, where the fold lines are located on a distal side and on a proximal side, taking the leaflet frame 231 from a ring or cylinder shape, and flattening it from a ring to a two-layer band i.e., folded over on itself, or like a cylinder flattened into a rectangle or square joined along two opposing sides. This allows the outer frame 102 and the flow control component 130 to reduce the radius along z-axis 109 until the side walls are in contact or nearly so. This also allows the outer frame 102 and the flow control component 130 to maintain the radius along the horizontal axis, the y-axis 108, to minimize the number of wire cells, which make up the outer frame 102 and the inner leaflet frame 231, that are damaged by forces applied during folding and/or compression necessary for loading into the delivery catheter.

The inner regurgitation control component 137, flow control component 130, leaflet frame 231, and the outer frame 102 are also vertically (y-axis) compressible, reducing the height of the entire valve 100 structure to fit within the inner diameter of a delivery catheter (not shown in this Figure). By folding in the z-axis 109 and vertically compressing in the y-axis 108, the valve structure is permitted to maintain a very large dimension along the horizontal, or x-axis 140. For example, a 60 mm or larger diameter valve can be delivered via transcatheter techniques. The length of the long axis of the valve 100, e.g., 60 mm, since it runs parallel to the central axis of the delivery catheter, is not limited by the large amount of wire frame and cover material necessary for such a large valve. This is not possible with existing center-axis delivery (axial) transcatheter valves. The use of a folded, compressed valve that is orthogonal to the traditional axial-delivery valves permits treatment options not available previously.

FIG. 1 also shows a distal anchoring tab 268 mounted on the distal side 118 of the annular outer support frame 102, and a proximal anchoring tab 270 mounted on the proximal side 114 of the annular outer support frame 102.

In a preferred embodiment, the horizontal x-axis 140 of the valve 100 is at an intersecting angle of between 45-135 degrees to the central vertical y-axis 108 when in an expanded configuration.

In a preferred embodiment, the horizontal x-axis 140 of the compressed configuration of the valve 100 is substantially parallel to a length-wise cylindrical axis of the delivery catheter.

In another preferred embodiment, the valve 100 has a height of about 5-60 mm and a diameter of about 25-80 mm.

FIG. 1 also shows guide wire sheath 310, and guide wire 311. A lumen or guide ball 266 is shown mounted on the distal end of the distal tab 268 and having the guide wire 311 threaded through the lumen 266. Although large enough in internal diameter to permit the guide wire 311 to extend through, the lumen 266 is not large enough in internal diameter to permit the sheath 310 to extend through. This allows sheath 310 to be advanced along the guide wire 311 until it runs up against the proximal side of the lumen 266, wherein continued application of a pushing force on the sheath 310 pushes against the lumen, and allows the valve 100 to be pulled by the distal tab 268 out of the delivery catheter, and to the target location for deploying the valve 100.

Figure 2:
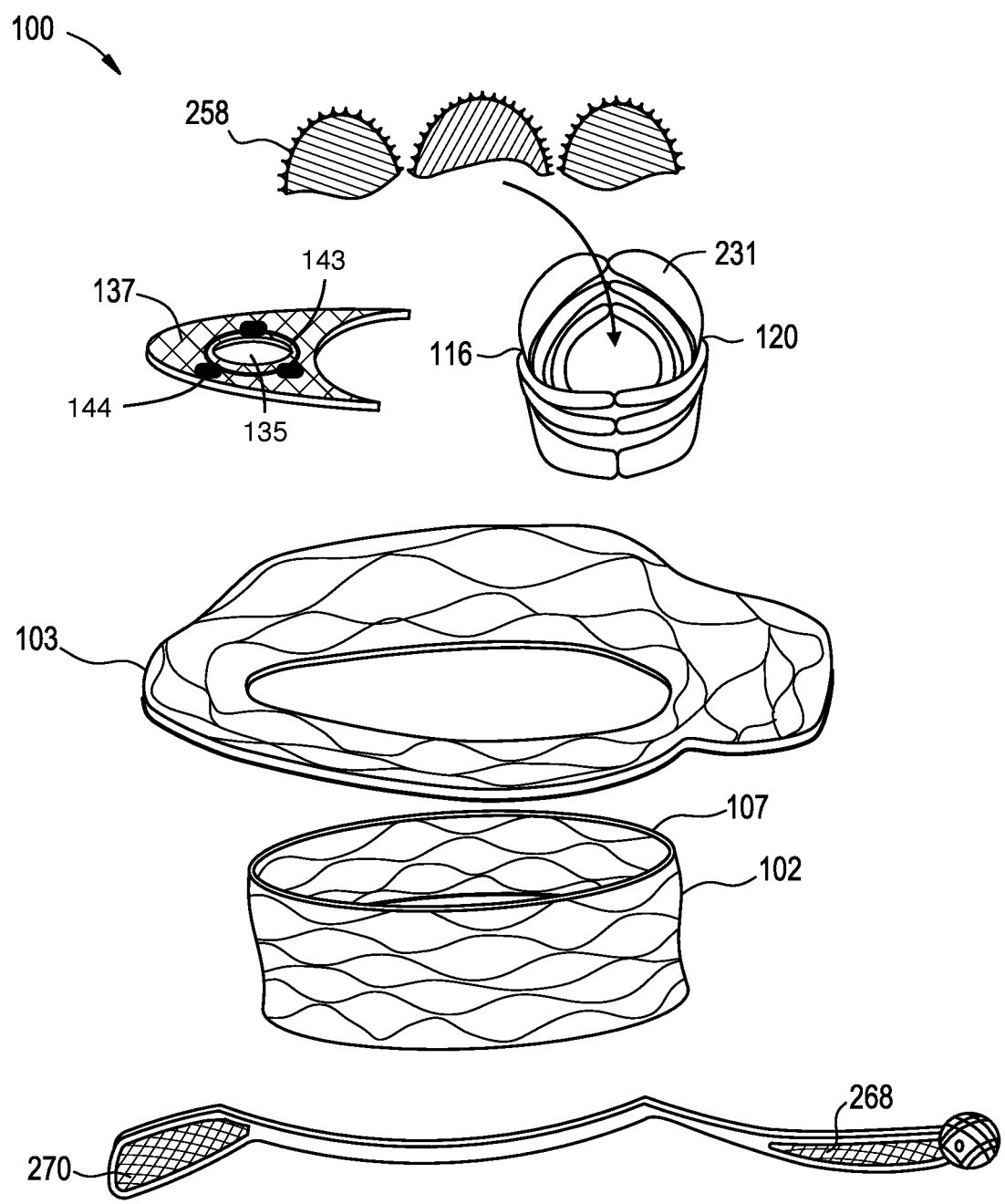

FIG. 2 is an illustration of a side perspective view of an exploded view of an embodiment having inner regurgitation component 137 with radio-opaque markers 144, drum channel 135, and reinforcement ring 143. FIG. 2 also shows three leaflets 258 (leaflet cusps or pockets) mounted within a foldable and compressible inner wire frame 231 (also referred to herein as "leaflet frame" and/or "inner leaflet frame"), with distal hinge point 120 (or fold area) and proximal hinge point 116 (or fold area), the inner leaflet frame 231 is mounted within an annular outer support frame 102 (also referred to herein as "outer wire frame," or "outer frame") which has a collar component 103 attached circumferentially at a top edge 107 of the outer frame 102, a dual tab component having a distal (RVOT) tab 268 and a proximal tab 270, and an optional mesh component of biocompatible material that may be used to cover the inner regurgitation control component 137, to cover the collar 103, to cover the inner and outer aspect of the outer frame 102, and/or to cover the anchoring tabs 268, and 270, according to the invention.

Atrial collar 103 is shaped to conform to the native deployment location. In a tricuspid replacement, the atrial collar will have a tall back wall portion to conform to the septal area of the native valve, and will have a distal and proximal upper collar portion. The distal collar portion can be larger than the proximal upper collar portion to account for the larger flat space above (atrial) the right ventricular outflow tract (RVOT) subannular area.

FIG. 3 is an illustration of a side perspective view of an orthogonally deliverable transcatheter heart valve 100 with an open regurgitation frame 139 having radio-opaque markers 144. In this embodiment, the drum channel 135 may have a predetermined interior diameter depending on the grade of regurgitation desired by the physician.

FIG. 3 also shows a collapsible flow control component 130 mounted within the annular outer support frame 102, the collapsible (inner) flow control component 130 having leaflet frame 231 with 2-4 flexible leaflets 258 mounted thereon. The leaflet frame 231 is foldable along a z-axis from a cylindrical configuration to a flattened cylinder configuration and compressible along a vertical axis (y-axis) to a shortened configuration. The valve 100 also has a superelastic wire loop distal tab 269 and a superelastic wire loop proximal tab 271 according to the invention.

Figure 4:
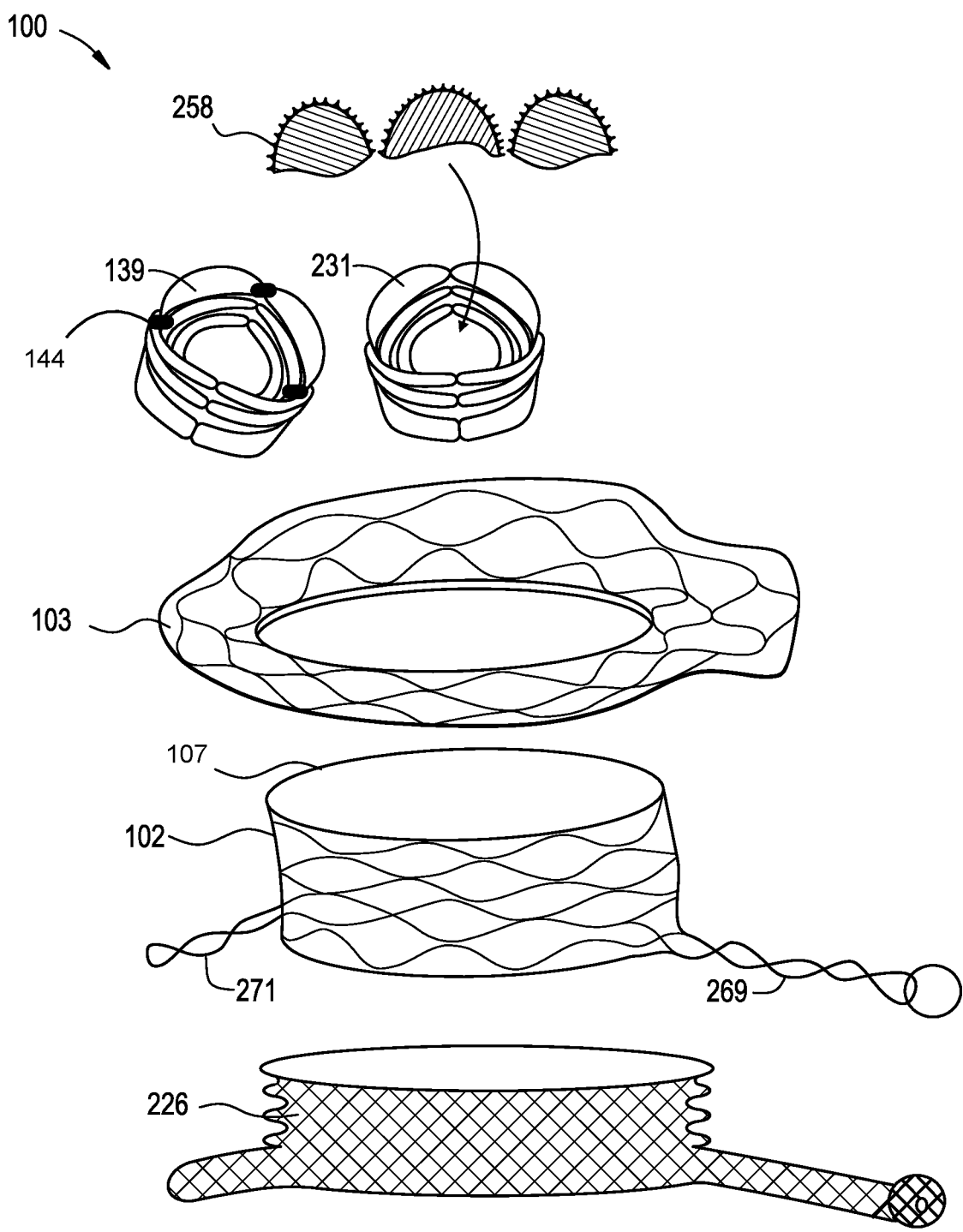

FIG. 4 is an illustration of a side perspective view of an exploded view of an embodiment having an open regurgitation frame 139 having radio-opaque markers 144. FIG. 4 also shows three leaflets 258 (leaflet cusps or pockets) mounted within a foldable and compressible inner wire frame 231 (also referred to as "leaflet frame"), the leaflet frame 231 is mounted within an annular outer support frame 102 (also referred to as "outer wire frame" or "outer frame") which has a collar component 103 attached circumferentially at a top edge 107 of the outer frame 102, a pair of integrated, independent tab components 269, 271, and a mesh component 226 (also referred to herein as "mesh sidewall cover" or "mesh cover"), according to the invention. Uncovered regurgitation frame 139 provides for controlled regurgitation of the valve. The uncovered regurgitation frame 139 can be later plugged with a later inserted stent or cover or plug once regurgitation is no longer needed by the patient.

Atrial collar 103 is shaped to conform to the native deployment location. In a tricuspid replacement, the atrial collar will have a tall back wall portion to conform to the septal area of the native valve, and will have a distal and proximal upper collar portion. The distal collar portion can be larger than the proximal upper collar portion to account for the larger flat space above (atrial) the right ventricular outflow tract (RVOT) subannular area.

Integrated tabs 269 and 271 are unitary construction with the body of the outer frame 102. The tabs may vary in size and shape. In a preferred embodiment, the RVOT tab, e.g., 269 may be longer to reach into the entry of the pulmonary artery (in the case of a tricuspid replacement).

Figure 5:
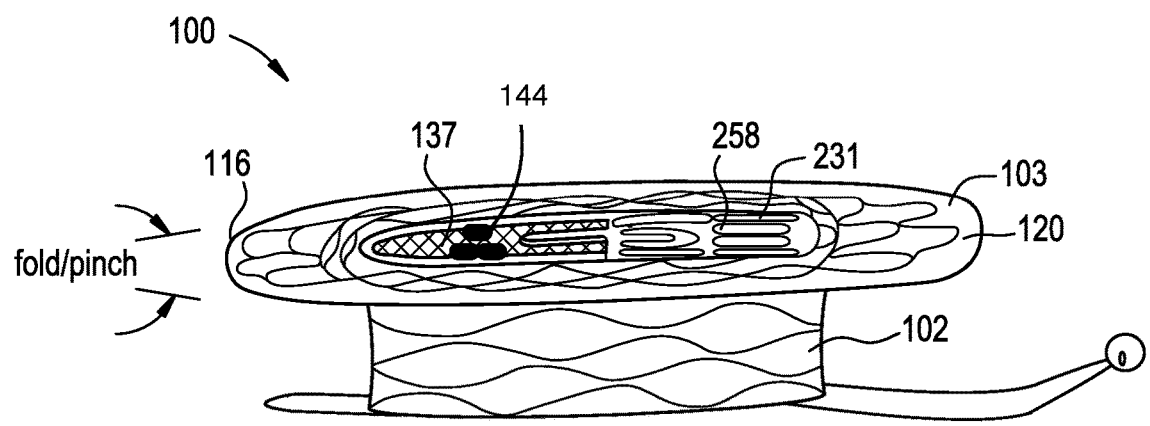
FIG. 5 is an illustration of a side perspective view of an orthogonally deliverable transcatheter heart valve in a folded configuration along the z-axis (front to back when viewed from the broader side) according to the invention.

FIG. 5 is an illustration of a side perspective view of an orthogonally deliverable transcatheter heart valve 100 in a folded configuration along the z-axis (front to back when viewed from the broader side) according to the invention. FIG. 5 shows a folded (flattened) outer frame 102 with folded/flattened collar 103, hinge points 116, 120. FIG. 5 also shows a folded/flattened inner regurgitation control component 137 with radio-opaque markers 144, and leaflets 258 mounted within a folded/flattened inner leaflet frame 231.

Figure 6:
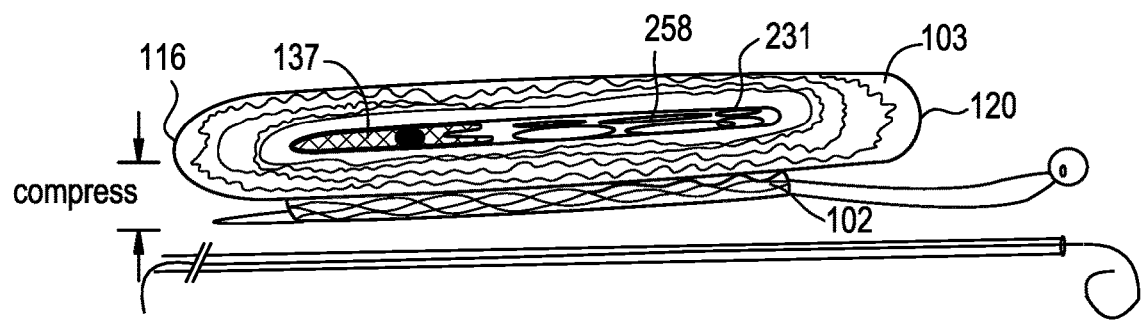
FIG. 6 is an illustration of a side perspective view of an orthogonally deliverable transcatheter heart valve in a vertically compressed configuration according to the invention.

FIG. 6 is an illustration of a side perspective view of an orthogonally deliverable transcatheter heart valve 100 in a vertically compressed configuration according to the invention. FIG. 6 shows the outer frame 102 folded (z-axis) and compressed vertically (y-axis) with the collar 103 folded (z-axis) and compressed (y-axis), along a fold line between hinge points 116, 120. FIG. 6 also shows an inner regurgitation control component 137, and leaflets 258 mounted within an inner leaflet frame 231.

Figure 7:
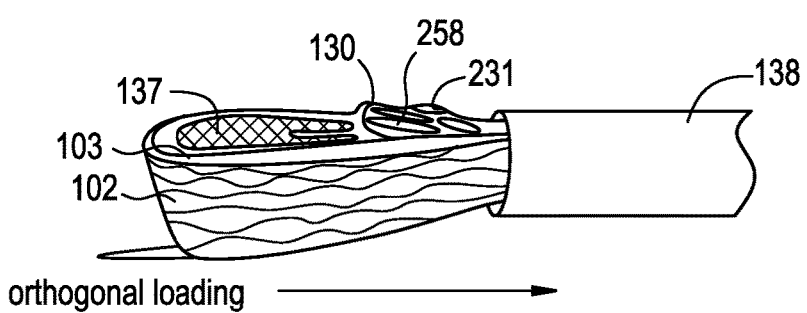
FIG. 7 is an illustration of a side perspective view of an orthogonally deliverable transcatheter heart valve partially loaded into a delivery catheter, according to the invention.

FIG. 7 is an illustration of a side perspective view of an orthogonally deliverable transcatheter heart valve 100 partially loaded into a delivery catheter 138, according to the invention. FIG. 7 shows an outer frame 102, a folded collar 103, an inner regurgitation control component 137, and a flow control component 130 having leaflets 258 and an inner leaflet frame 231.

Figure 8:
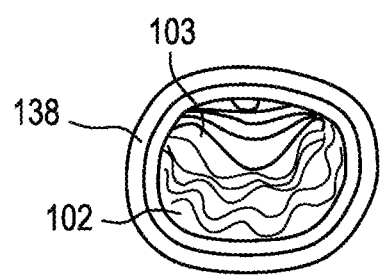
FIG. 8 is an illustration of an end view of a delivery catheter showing the loaded valve, according to the invention.

FIG. 8 is an illustration of an end view of the delivery catheter 138 showing the loaded valve 100 with outer frame 102 and collar 103 visible, according to the invention.

Figure 9:
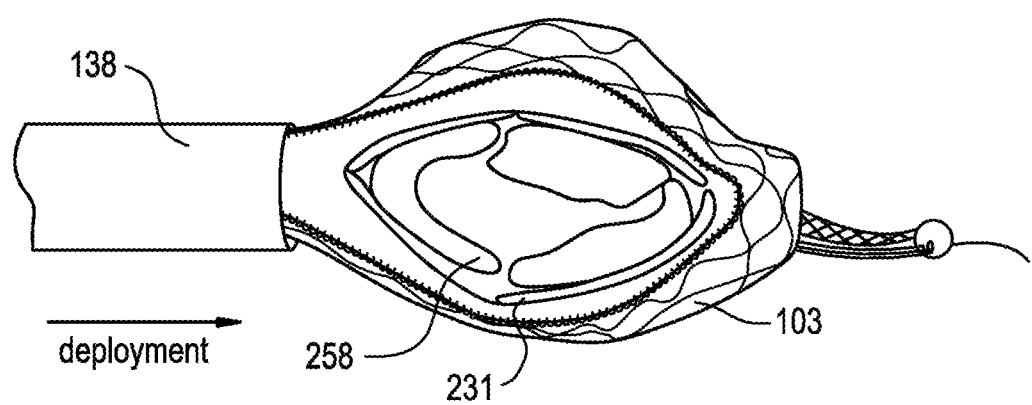
FIG. 9 is an illustration of a top view of the folded, compressed valve being expelled from the delivery catheter, in a partial position to allow expansion of the leaflets and the inner leaflet frame prior to seating in the native annulus.

FIG. 9 is an illustration of a top view of the folded, compressed valve 100 being expelled from the delivery catheter 138, in a partial position to allow expansion of the leaflets 258, the collar 103, and the inner leaflet frame 231 prior to seating in the native annulus.

Figure 10:
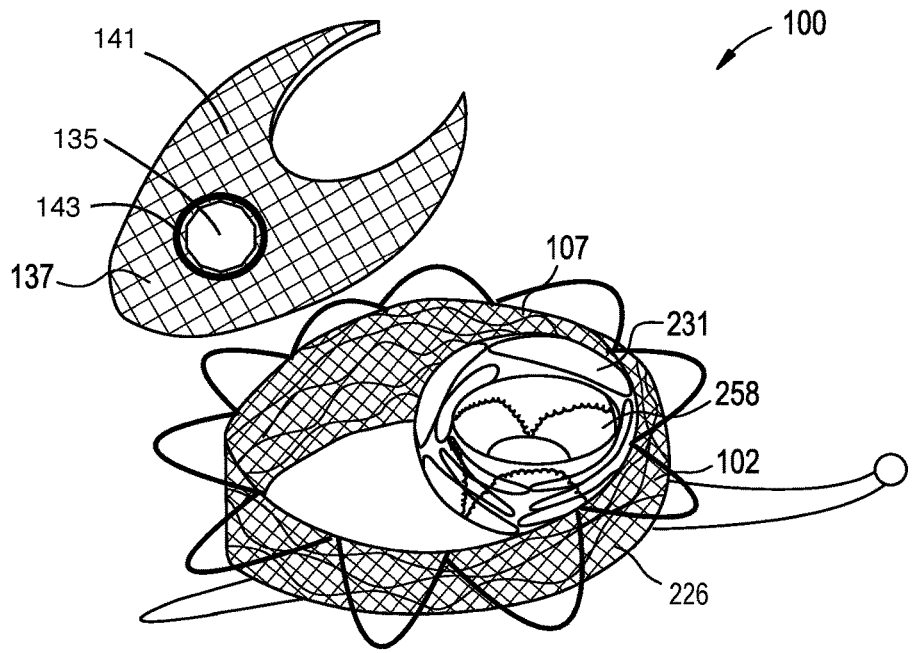
FIG. 10 is an illustration of a top perspective view of a valve having an inner regurgitation control component as part of a mesh spacer frame which is shown removed for viewing, an outer frame with a mesh sidewall cover, an inner leaflet frame, and leaflets sewn into the inner leaflet frame, according to the invention.

FIG. 10 is an illustration of a top perspective view of a valve 100 without a collar having an inner regurgitation control component 137 removed for viewing, with a tissue cover 141, a reinforcement ring 143 and a drum channel 135 shown. FIG. 10 also shows an outer frame 102 with a mesh sidewall cover 226, an inner leaflet frame 231, and leaflets 258 sewn into the inner leaflet frame 231, according to the invention.

Figure 11:
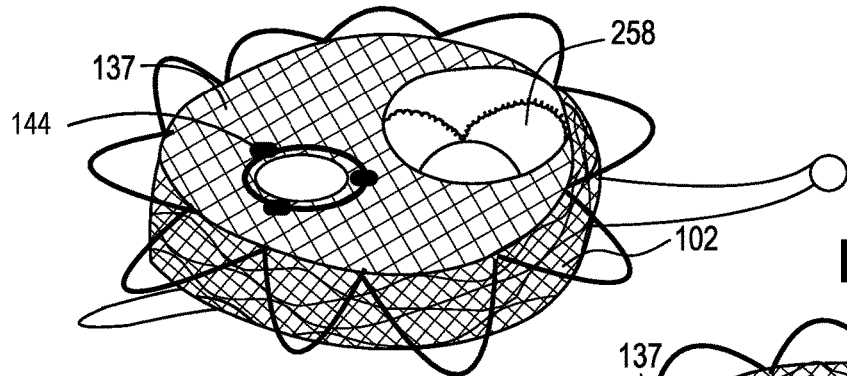
FIG. 11 is an illustration of a top perspective view of a valve having an inner regurgitation control component with radio-opaque markers as part of a mesh spacer frame mounted on the top edge of the outer frame, the outer frame also having a mesh sidewall cover, an inner leaflet frame, and leaflets sewn into the inner leaflet frame, according to the invention.

FIG. 11 is an illustration of a top perspective view of a valve 100 without a collar having markers 144, and an inner regurgitation control component 137 mounted on the top edge 107 of the outer frame 102, the outer frame 102 also having a mesh sidewall cover 226, an inner leaflet frame 231, and leaflets 258 sewn into the inner leaflet frame 231, according to the invention.

Figure 12:
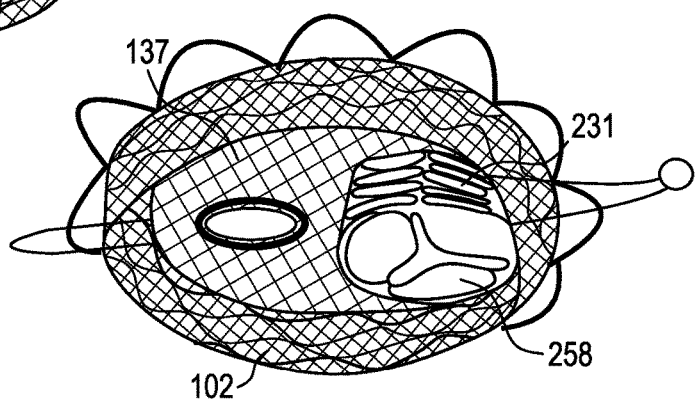
FIG. 12 is an illustration of a bottom perspective view of a valve having an inner regurgitation control component as part of a mesh spacer frame mounted on the top edge of the outer frame, the outer frame also having a mesh sidewall cover, an inner leaflet frame, and leaflets sewn into the inner leaflet frame, according to the invention.

FIG. 12 is an illustration of a bottom perspective view of a valve 100 without a collar having an inner regurgitation control component 137 mounted on the top edge 107 of the outer frame 102, the outer frame 102 also having a mesh sidewall cover 226, an inner leaflet frame 231, and leaflets 258 sewn into the inner leaflet frame 231, according to the invention.

Figure 13:
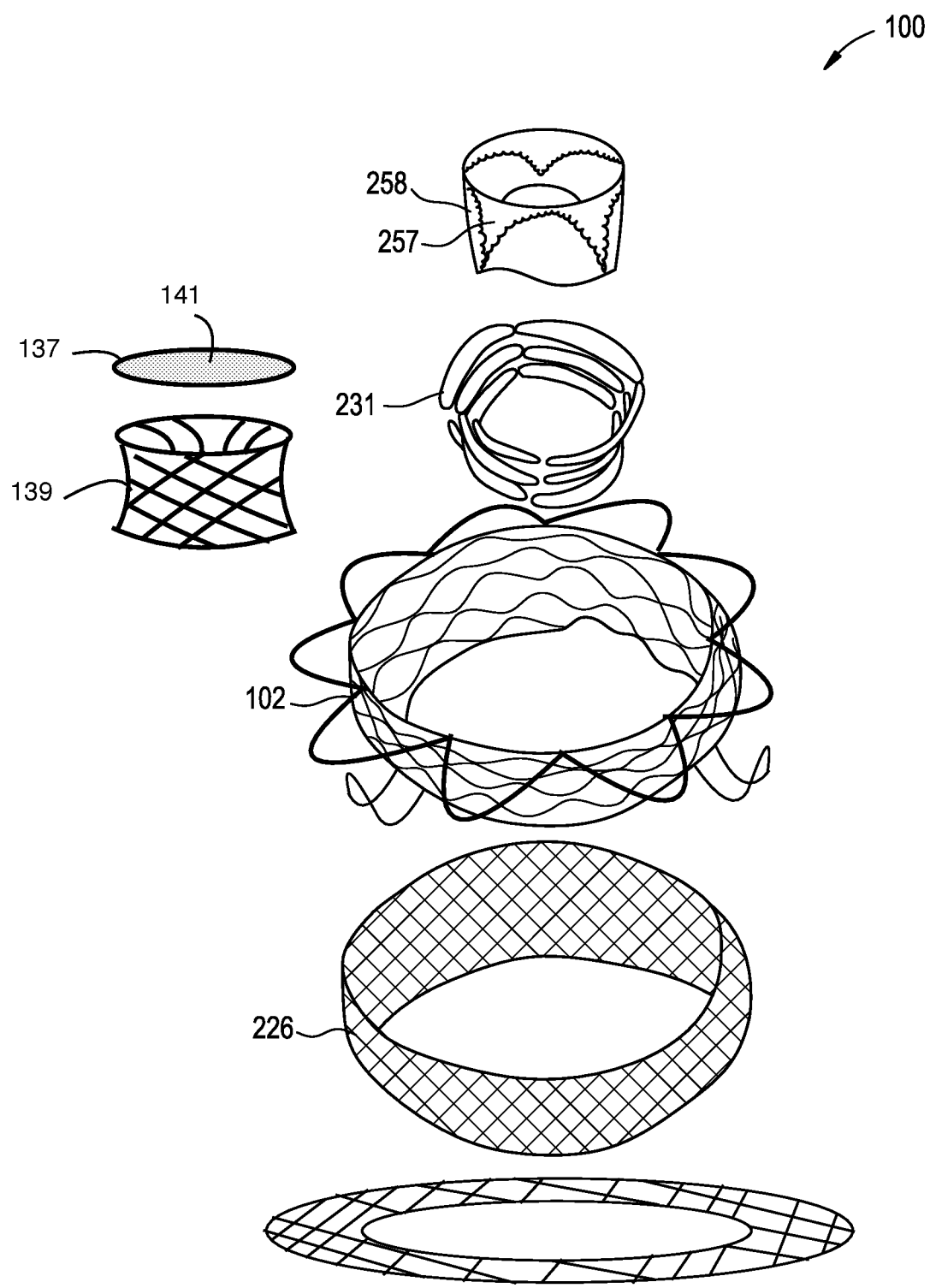
FIG. 13 is an illustration of an exploded view of a valve having an inner regurgitation control component, an outer frame, the outer frame having a mesh sidewall cover, an inner leaflet frame, and leaflets sewn into the inner leaflet frame, according to the invention.

FIG. 13 is an illustration of an exploded view of a valve without a collar having an inner regurgitation control component 137 comprising a tissue cover 141 and a regurgitation frame 139. FIG. 13 also shows an outer frame 102, the outer frame 102 having a mesh sidewall cover 226, an inner leaflet frame 231, and leaflets 258 mounted on a structural band 257 (also referred to herein as "band") and sewn into the inner leaflet frame 231, according to the invention.

Figure 14:
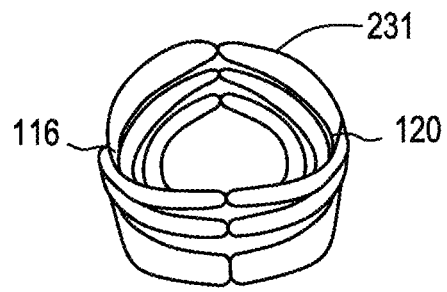
FIG. 14 is an illustration of a top perspective view of an inner leaflet frame in a cylinder configuration, shown at the beginning of a process permitting folding and compression of the inner leaflet frame, according to the invention.

FIG. 14 is an illustration of a top perspective view of an inner leaflet frame 231 (or a regurgitation frame), in a cylinder configuration, shown at the beginning of a process permitting folding and compression of the inner leaflet frame, according to the invention.

Figure 15:
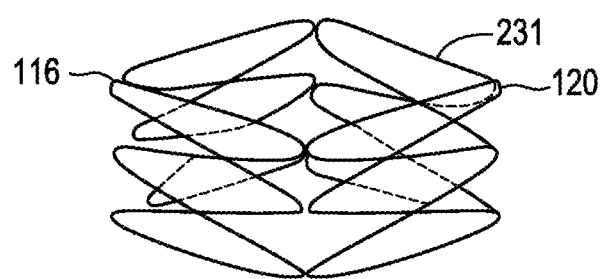
FIG. 15 is an illustration of a top perspective view of an inner leaflet frame in a partially folded configuration with the wireframe sidewalls rotating or hinging at their lateral connection points, shown as a partial first step in a process permitting folding and compression of the inner leaflet frame, according to the invention.

FIG. 15 is an illustration of a top perspective view of an inner leaflet frame 231 (or a regurgitation frame) in a partially folded configuration with the wireframe sidewalls rotating or hinging at their lateral connection points 116, 120 (also referred to as "hinge points"), shown as a partial first step in a process permitting folding and compression of the inner leaflet frame 231, according to the invention.

Figure 16:
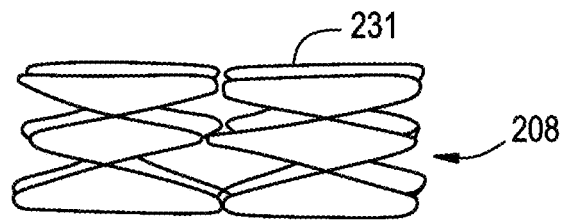
FIG. 16 is an illustration of a side view of an inner leaflet frame in a completely folded configuration with the wireframe sidewalls rotated or hinged at their lateral connection points, shown as a completed first step in a process permitting folding and compression of the inner leaflet frame, according to the invention.

FIG. 16 is an illustration of a side view of an inner leaflet frame 231 (or a regurgitation frame) in a completely folded configuration 208 with the wireframe sidewalls rotated or hinged at their lateral connection points, shown as a completed first step in a process permitting folding and compression of the inner leaflet frame 231, according to the invention.

Figure 17:
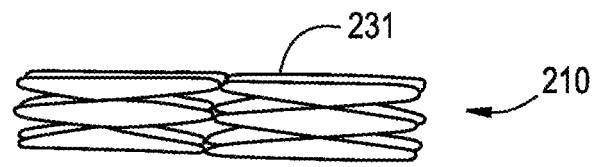
FIG. 17 is an illustration of a side view of an inner leaflet frame in a folded and vertically compressed configuration with the wireframe sidewalls vertically compressed in a pleated or accordion configuration, shown as a second step in a process permitting folding and compression of the inner leaflet frame, according to the invention.

FIG. 17 is an illustration of a side view of an inner leaflet frame 231 (or a regurgitation frame) in a folded and vertically compressed configuration 210 with the wireframe sidewalls vertically compressed in a pleated or accordion configuration, shown as a second step in a process permitting folding and compression of the inner leaflet frame 231, according to the invention.

Figure 18:
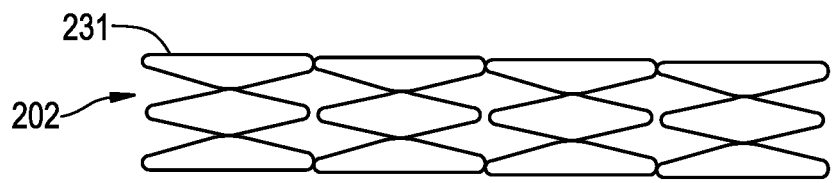
FIG. 18 is an illustration of a side view of an inner leaflet frame as a linear wireframe sheet before further assembly into a cylinder structure, according to the invention.

FIG. 18 is an illustration of a side view of an inner leaflet frame 231 (or a regurgitation frame) as a linear wireframe sheet 202 before further assembly into a cylinder structure, according to the invention.

Figure 19:
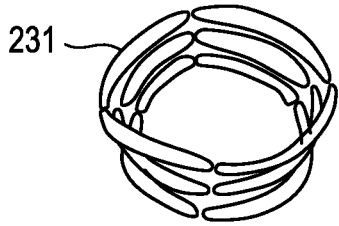
FIG. 19 is an illustration of a side perspective view of an inner leaflet frame in a cylinder or cylinder-like (conical, etc.) configuration, according to the invention.

FIG. 19 is an illustration of a side perspective view of an inner leaflet frame 231 in a cylinder or cylinder-like (conical, etc.) configuration, according to the invention.

Figure 20:
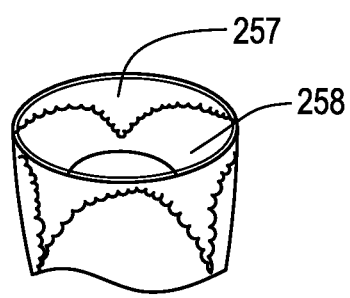
FIG. 20 is an illustration of a side perspective view of a band of pericardial tissue that is configured in a cylinder shape with leaflet pockets sewn into a structural band, according to the invention.

FIG. 20 is an illustration of a side perspective view of a band of pericardial tissue 257 (also referred to herein as a "structural band") that is configured in a cylinder shape with leaflets 258 (also referred to herein as "leaflet pockets") sewn into the structural band 257, according to the invention.

Figure 21:
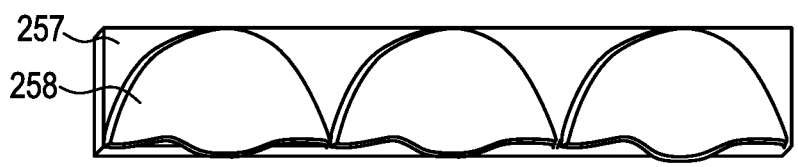
FIG. 21 is an illustration of a side view of a band of pericardial tissue with leaflet pockets sewn into a structural band, before assembly into a cylindrical leaflet component and mounting on an inner leaflet frame to form a collapsible (foldable, compressible) flow control component, according to the invention.

FIG. 21 is an illustration of a side view of a band of pericardial tissue 257 with leaflet pockets 258 sewn into the structural band 257, before assembly into a cylindrical leaflet component and mounting on an inner leaflet frame to form a collapsible (foldable, compressible) flow control component, according to the invention.

Figure 22:
FIG. 22 is an illustration of a bottom view of a band of pericardial tissue with leaflet pockets sewn into a structural band, before assembly into a cylindrical leaflet component and mounting on an inner leaflet frame to form a collapsible (foldable, compressible) flow control component, according to the invention.

FIG. 22 is an illustration of a bottom view of a band of pericardial tissue 257 with leaflet pockets 258 sewn into the structural band 257, before assembly into a cylindrical leaflet component and mounting on an inner leaflet frame to form a collapsible (foldable, compressible) flow control component, according to the invention.

Figure 23:
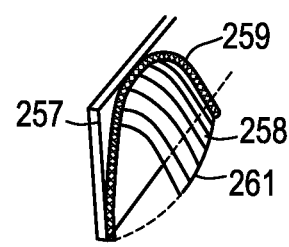
FIG. 23 is an illustration of a side perspective view of part of a band of pericardial tissue with a single leaflet pocket sewn into a structural band, showing an open bottom edge and a sewn, closed top parabolic edge, according to the invention.

FIG. 23 is an illustration of a side perspective view of part of a band of pericardial tissue 257 with a single leaflet pocket 258 sewn into the structural band 257, showing partial coaptation of the leaflet pocket 258 with open edge 261 extending out and a sewn edge 259 as a closed top parabolic edge providing attachment, according to the invention.

Figure 24:
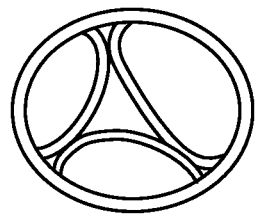
FIG. 24 is an illustration of a bottom view of a cylindrical leaflet component showing partial coaptation of the leaflets to form a closed fluid-seal, according to the invention.

FIG. 24 is an illustration of a bottom view of a cylindrical leaflet component showing complete coaptation, to form a closed fluid-seal, according to the invention.

Figure 25A:
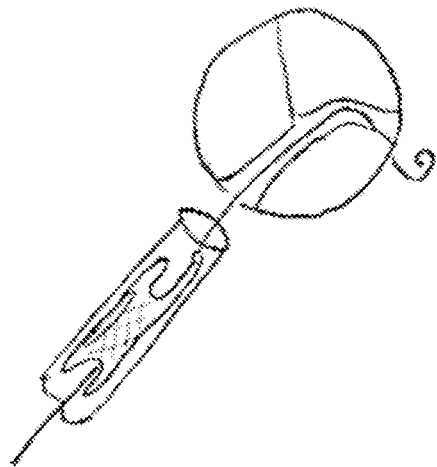
FIGS. 25A-25E are illustrations of a process whereby a valve having a pre-perforated drum inner is orthogonally delivered within the catheter, expelled from the catheter, and deployed into the native annulus.
Figure 25B:
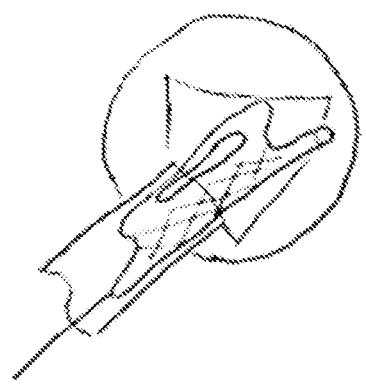
Figure 25C:
Figure 25D:
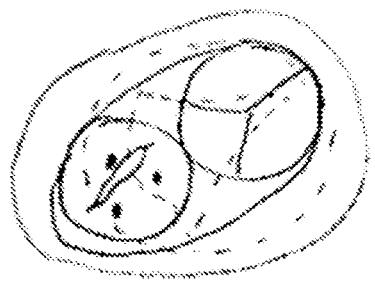
Figure 25E:
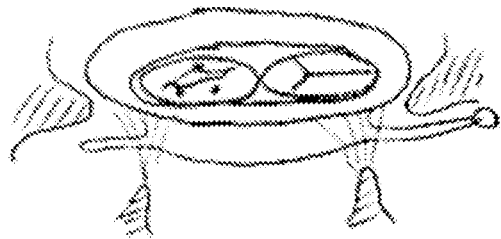

FIGS. 25A-25E are illustrations of a process whereby a valve having a pre-perforated drum inner is orthogonally delivered within the catheter, expelled from the catheter, and deployed into the native annulus. FIG. 25A shows a compressed and folded orthogonal valve within a delivery catheter and moving along a guide wire through a native annulus. FIG. 25B shows an orthogonal being partially expelled into the native annulus, with the delivery catheter able to torque or position the valve, as necessary. FIG. 25C shows a fully expelled valve with a RVOT tab extending subannularly to help anchor the valve and the valve held up at an angle to allow for washing and coaptation to be implemented/commenced. FIG. 25D is a top view showing the pre-perforated drum and regurgitation channel located within the perimeter of the radio-opaque markers. FIG. 25E is a side perspective view and shows the pre-perforated drum and regurgitation channel located within the perimeter of the radio-opaque markers, the inner regurgitation control component mounted within the outer support frame, adjacent the inner flow control component (leaflets and frame).

Figure 26:
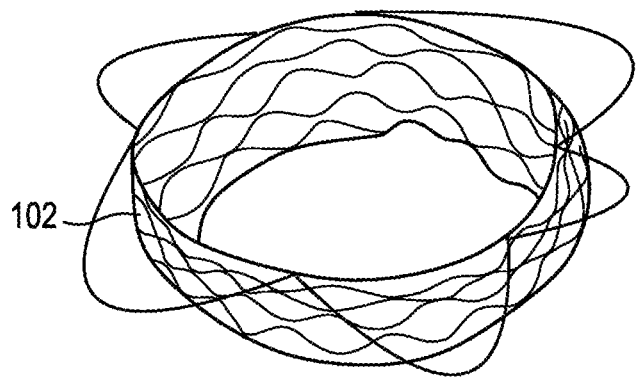
FIG. 26 is an illustration of a top perspective view of an outer frame in a cylinder configuration, shown at the beginning of a process permitting folding and compression of the outer frame, according to the invention.

FIG. 26 is an illustration of an outer frame 102 (also referred to as "outer wire frame").

Figure 27:
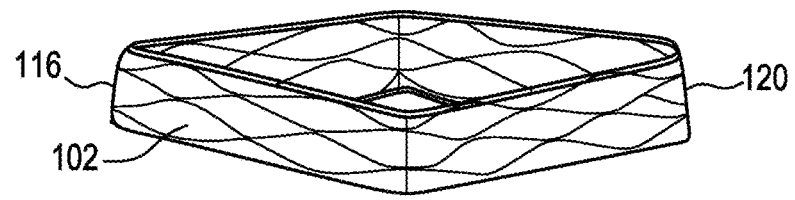
FIG. 27 is an illustration of a top perspective view of an outer frame in a partially folded configuration with the wireframe sidewalls rotating or hinging at their lateral connection points, shown as a partial first step in a process permitting folding and compression of the outer frame, according to the invention.

FIG. 27 is an illustration of a top perspective view of a partially folded configuration of the outer wireframe 102 with sidewalls rotating or hinging at their lateral connection points 116, 120 (hinge points), shown as a partial first step in a process permitting folding and compression of the outer frame 102, according to the invention.

Figure 28:
FIG. 28 is an illustration of a side view of an outer frame in a completely folded flat configuration with the wireframe sidewalls rotated or hinged at their lateral connection points, shown as a completed first step in a process permitting folding and compression of the outer frame, according to the invention.

FIG. 28 is an illustration of a side view of an outer frame 102 in a completely folded, flat configuration 208 with the wireframe sidewalls rotated or hinged at their lateral connection points 116, 120 (hinge points), shown as a completed first step in a process permitting folding and compression of the outer frame 102, according to the invention.

Figure 29:
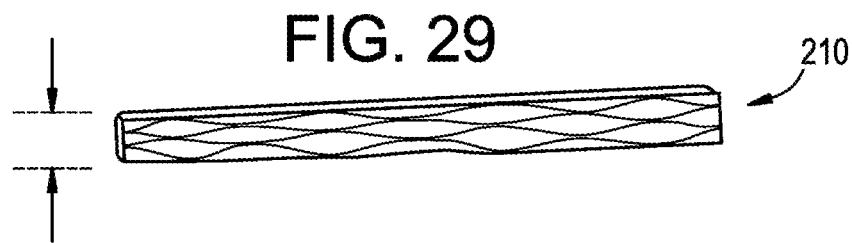
FIG. 29 is an illustration of a side view of an outer frame in a folded and vertically compressed configuration with the wireframe sidewalls vertically compressed in a pleated or accordion configuration, shown as a second step in a process permitting folding and compression of the outer frame, according to the invention.

FIG. 29 is an illustration of a side view of an outer frame 102 in a folded and vertically compressed configuration 210 with the wireframe sidewalls vertically compressed in a pleated or accordion configuration, shown as a second step in a process permitting folding and compression of the outer frame 102, according to the invention.

FIG. 30 is an illustration of a top perspective view of an assembled valve 100 with an inner regurgitation control component 137 having markers and a reinforcing ring, an outer frame 102, a flow control component 130 having an inner leaflet frame 231 and three leaflets 258 (leaflet pockets/cusps), an inner spacer frame 139, and a tissue cover 141 over the spacer frame 139, fold-line 109 is shown as a dashed line, according to the invention.

FIG. 31 is an illustration of a top perspective view of an assembled valve 100 with an inner regurgitation control component 137 having markers, an outer frame 102, a first sub-annular anchoring/positioning tab 268 mounted on the outer frame 102 adjacent the flow control component 130, a second sub-annular anchoring/positioning tab 270 mounted on the outer frame 102 in a different location, the flow control component 130 having an inner leaflet frame and three leaflets 258 (leaflet pockets/cusps), an inner spacer frame 139, and a tissue cover 141 over the spacer frame 139, fold-line 109 is shown as a dashed line and crosses the tissue cover 141, according to the invention.

FIG. 32 is an illustration of a bottom perspective view of an assembled valve 100 with an outer frame 102, a first sub-annular anchoring/positioning tab 268 mounted on the outer frame 102 adjacent the flow control component 130, a second sub-annular anchoring/positioning tab 270 mounted on the outer frame 102 in a different location, the flow control component 130 having an inner leaflet frame 231 and three leaflets 258 (leaflet pockets/cusps), an inner spacer frame 139 and a tissue cover 141 over the spacer frame 139, fold-line 109 is shown as a dashed line, and hemodynamic washing cavity is shown under the covered inner spacer frame 139, according to the invention.

FIG. 33 is an illustration of a top view of an assembled valve 100 with an inner regurgitation control component 137, an outer frame 102, a flow control component 130 having an inner leaflet frame 231 and three leaflets 258 (leaflet pockets/cusps), an inner spacer frame 139, and a tissue cover 141 over the spacer frame 139, according to the invention.

FIG. 34 is an illustration of a top view of an assembled valve 100 with an inner regurgitation control component 137 having reinforcement ring, an outer frame 102, a first sub-annular anchoring/positioning tab 268 mounted on the outer frame 102 adjacent the flow control component 130, a second sub-annular anchoring/positioning tab 270 mounted on the outer frame 102 in a different location, the flow control component 130 having an inner leaflet frame 231 and three leaflets 258 (leaflet pockets/cusps), an inner spacer frame 139, and a tissue cover 141 over the spacer frame 139, according to the invention.

FIGS. 35A-35E is an illustration of a step by step process where the tissue drum is perforated prior to loading the valve orthogonally into the delivery catheter. FIG. 35A shows a step of providing an orthogonal prosthetic valve as described herein (foldable, compressible for sideways delivery with RVOT tab, guide wire lumen, atrial collar, and proximal tab). FIG. 35B shows a step of creating an opening by cutting or using a balloon device. FIG. 35C shows a step of folding the valve flat to prepare for loading into the delivery catheter. FIG. 35D shows a step of vertically compressing the valve to prepare for loading the valve into the delivery catheter.

FIG. 35E shows a step of loading the orthogonal valve sideways into the delivery catheter.

FIGS. 36A-36C is an illustration of a step by step process where the tissue drum is perforated after the valve is expelled orthogonally from the delivery catheter, and deployed into the native annulus. FIG. 36A shows a step of expelling the valve into the native annulus, approaching horizontally at a slightly raise angle to position the RVOT tab into the subannular space leading to the right (pulmonary) valve outflow tract. FIG. 36B shows a step of locating the radio-opaque markers using fluoroscopy. FIG. 36C shows a step of creating an opening by cutting or using a balloon device.

FIG. 37 is an illustration of how a user can match the size of the aperture to the amount of regurgitation desired, e.g., a range from 0.5-2.0 grades of regurgitation. Radio-opaque markers can be used to aide in measuring how large of a perforation to make.

FIG. 38 is an illustration of how a user can match the size of the lumen of a tubular stent that can be deployed into the aperture to match the amount of regurgitation desired, e.g., a range from 0.5-2.0 grades of regurgitation.

FIG. 39 is an illustration of a side septal plan view of a valve 100 with sub-annular anchoring and/or positioning tab 268 extending towards a distal side, and second sub-annular tab 270 extending away to a proximal side, and with foldable and compressible wireframe construction visible (outer frame 102), including inner leaflet frame 231, leaflets 258, and inner regurgitation control component 137, according to the invention.

Figure 40:
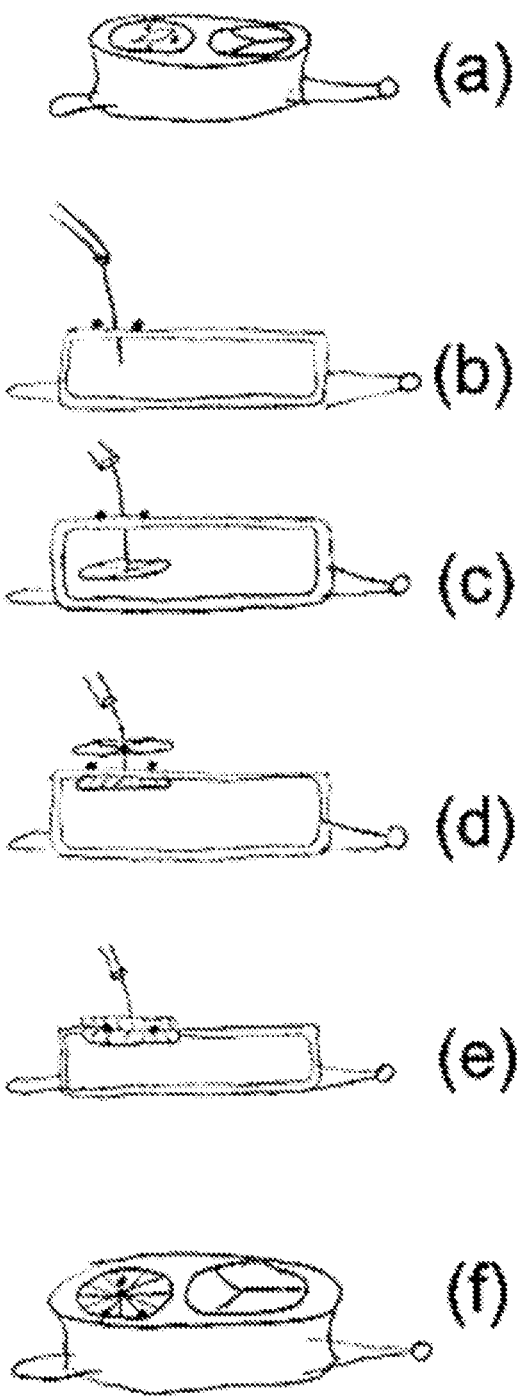

FIGS. 40A-40F is an illustration of a closure device used to close a perforation in an inner regurgitation control component. FIG. 40A shows a step of providing an orthogonal prosthetic valve as described herein (foldable, compressible for sideways delivery with RVOT tab, guide wire lumen, atrial collar, and proximal tab) that has an inner regurgitation control component in need of sealing off. FIG. 40B shows a step of accessing the perforation using a catheter tool.

FIG. 40C shows a step of expanding a first disk or button on the distal, underside of the perforation. FIG. 40D shows a step of expanding a second disk or button on the proximal, top-side of the perforation. FIG. 40E shows a step of cinching the two disks/buttons together, creating a seal to stop the regurgitation that was engineered in the, e.g., 1-2 mm perforation. FIG. 40F shows a step of withdrawing the catheter tool.

FIG. 41 is an illustration of a top view of a valve 100 partially expelled from a delivery catheter 138, with a distal tab 268 leading the valve 100 (along guide wire not shown) to the deployment location, with distal flow control component 130 beginning to open and showing two of three leaflets 258 opening from a folded, lie-flat configuration with the third leaflet opening from a folded configuration where it is folded back on itself when in the delivery catheter 138.

FIG. 42 is an illustration of a top view of a valve compressed 136 (orthogonally loaded) within a delivery catheter 138 with an outer frame 102 having a first tab 268 extending forward along an x-axis and a second trailing tab 270 extending backwards along the x-axis.

FIG. 43 is an illustration of a top view of a valve 100 having an outer frame 102, an off-center inner flow control component 130 (leaflet in frame) and an irregularly shaped spacer/support frame 139A, according to the invention.

FIG. 44 is an illustration of a top view of a valve 100 having an outer frame 102, a centrally located inner flow control component 130 (leaflet in frame) and a pair of irregularly shaped spacer/support frames 139A, 139B on opposing sides of the inner flow control component 130, according to the invention.

FIG. 45 is an illustration of a top view of a valve 100 having an outer frame 102, and an inner flow control component 130 (leaflet in frame) and a plurality of sewn attachment points 129 where the inner flow control component 130 is sewn to the outer frame 102, according to the invention.

FIG. 46 is an illustration of a top view of a valve 100 having an inner regurgitation control component 137 with a pacemaker and lead wire set 145 extending through a perforation. FIG. 46 also shows an outer frame 102, an off-center inner flow control component 130 having an inner leaflet frame 231 and leaflets 258, and an inner spacer frame 139, all three structures foldable along the same x-axis 109, according to the invention.

FIG. 47 is an illustration of a top view of a valve 100 having an outer frame 102, a centrally positioned inner flow control component 130 having an inner leaflet frame 231 and leaflets 258, and a pair of smaller cylindrical inner regurgitation control components 137, 147 mounted on opposing sides of the inner flow control component 130 to provide support within the interior dimension of the outer frame 102, all four structures foldable along the same x-axis 109, according to the invention. Here, the first inner regurgitation control component 137 has a three-leaflet mini-valve mounted adjacent next to the main flow control component 130, and the second inner regurgitation control component 147 has an un-perforated tissue cover, which may later provide an opportunity for a practitioner to add additional regurgitation as necessary.

FIG. 48 is an illustration of a top view of a valve 100 having a distal side inner regurgitation control component 137, an outer frame 102, and a proximally located off-set inner flow control component 130 having an inner leaflet frame 231 and leaflets 258, all three structures foldable along the same x-axis 109, according to the invention.

FIG. 49 shows orthogonal delivery steps: (1) provide a foldable, compressible prosthetic tricuspid valve; (2) load the valve sideways into a delivery catheter 138; (3) advance the valve to the heart via the IVC or the SVC over a pre-placed guidewire that is threaded onto a subannular distal tab; (4) partially expel the valve to position the distal subannular tab and to allow the valve leaflets to begin functioning; (5) complete deployment of the valve into the native annulus. (6) Optionally: if the regurgitation drum was not opened prior to loading into the delivery catheter, a cutting tool or balloon tool can be advanced, and a 1-2 mm opening is made in the tissue covering of the drum frame. (7) Optionally: a pacemaker wire set can be advanced through the opening in the regurgitation drum and the pacemaker wire(s) attached at or near the target nodes.

ADDITIONAL DEFINITIONS AND PARTS LIST

Below is provide a parts list in relation to claimed elements. Part numbering may refer to functional components and may be re-used across differing preferred embodiments to aid in uniformly understanding structure-function relationships. To avoid cluttering in drawing sheets, not every number may be added to the drawing sheets.

100 Dual-tab orthogonally delivered transcatheter prosthetic heart valve.
102 Self-expanding annular (outer) support frame.
103 Collar structure.
104 Central channel.
106 Outer perimeter wall.
107 Top edge of outer support frame.
108 Central vertical axis.
109 Z-axis, front to back, fold line axis.
110 Front wall portion of perimeter wall.
112 Back wall portion of perimeter wall.
114 Proximal side.
116 Proximal fold area.
117 Secondary proximal fold areas.
118 Distal side.
120 Distal fold area.
121 secondary distal fold areas.
122 Front upper collar portion.
124 Front lower body portion of outer frame.

126 Back upper collar portion.
128 Back lower body portion.
129 Sewn attachment points for inner to outer.
130 Flow control component, made of an inner frame having tissue leaflets mounted therein, collapsible (foldable and compressible), the inner mounted within the annular outer support frame and configured to permit blood flow in a first direction through an inflow end and block blood flow in the opposite, second direction, through the outflow end.
132 Inflow end.
134 Outflow end.
135 Drum channel.
136 Compressed configuration
137 Inner regurgitation control component.
138 Delivery catheter.
139 Uncovered regurgitation frame, engineered (therapy) partial regurgitation
140 X-axis, a horizontal axis, parallel to delivery, catheter central axis
141 Tissue cover (plastic deformation).
142 Intersecting angle 45-135 degrees, X-axis to Y-axis.
143 Reinforcement ring.
144 Radio-opaque markers.
146 Length-wise cylindrical axis of delivery catheter.
148 Height of about 5-60 mm.
150 Diameter of about 25-80 mm.
202 Plurality of compressible wire cells—outer frame.
204 Orientation and cell geometry substantially orthogonal to the central vertical axis to minimize wire cell strain when the annular support frame is compressed.
206 Vertical compressed configuration.
208 Folded configuration.
210 Folded and compressed configuration.
212 Inner frame or outer frame shape selected from a funnel, cylinder, flat cone, or circular hyperboloid.
220 Braided matrix.
222 Wire frame matrix.
224 Laser-cut wire frame.
226 Biocompatible material.
227 Flared cuff on inner frame.
228 Side profile of inner frame as a flat cone shape.
229 Non-cylindrical inner frame, e.g., elliptical section.
230 Diameter R of 40-80 mm.
231 Inner frame, for mounting leaflets.
232 Diameter r of 20-60 mm.
233 Set of uniform wire frame cells of inner.
234 Height of 5-60 mm.
235 Non-uniform variable height cells of inner.
236 Interior surface of annular outer support frame.
237 Non-uniform cell geometries, sizes in wire frame.
238 Exterior surface of annular outer support frame.
239 Compressed inner.
240 Pericardial tissue for covering valve surfaces.
241 Diamond or eye-shaped wire cells.
242 Woven synthetic polyester material.
243 Eyelets on inner wire frame, consistent commissure attachment.
244 Outer support frame with an hourglass shape.
245 Laser cut attachment feature on inner frame.
246 Top diameter R1 of 40-80 mm.
248 Bottom diameter R2 of 50-70 mm.
250 Internal diameter r of 20-60 mm.
252 Height of 5-60 mm.
254 Internal diameter of 20-60 mm.
256 Height of 10-40 mm.
257 Leaflet band, mounting band for leaflet pockets.
258 Leaflets, plurality of leaflets, pericardial material.
259 Sewn edge of leaflet.
260 Rounded cylinder at an inflow end.
261 Open edge of leaflet
262 Flat closable aperture at an outflow end.
264 Longitudinal supports in/on flow control component, selected from rigid or semi-rigid posts, rigid or semi rigid ribs, rigid or semi-rigid battons, rigid or semi rigid panels, and combinations.
266 (any) lumen (ball) on distal tab.
268 Distal tab/sub-annular anchoring tab, can be RVOT or other, comprised of wire loop or wire frame, integrated frame section, or stent, extending from about 10-40 mm away from the annular support frame.
269 Independent RVOT tab.
270 Proximal tab/sub-annular anchoring tab.
271 Independent proximal tab.
272 Distal upper edge of the annular support frame.
273 Upper atrial tension arm comprised of wire loop or wire frame extending from about 2-20 mm
away from the annular support frame.
274 Lower tension arm comprised of wire loop or wire frame, integrated frame section, or stent, extending from about 10-40 mm away from the annular support frame.
276 Distal side of the annular support frame.
278 Tissue anchors connected to the annular support frame for engaging native tissue.
280 Front wall portion of frame is a first flat panel.
282 Back wall portion of frame is a second flat panel.
284 Sewn seam.
285 Hinge.
286 Flexible fabric span without any wire cells.
287 Fabric panel.
288 Braided-wire cells.
289 Commissure attachment—leaflet to frame.
290 Laser-cut wire cells.
302 Rolling into a compressed configuration.
304 Bilaterally roll compressed configuration.
306 Flattening the annular support frame panels.
308 Compressed annular support frame from top to bottom.
310 Sheath/Rigid elongated pushing rod/draw wire.
311 Guide wire.
312 Steerable catheter for rotating the heart valve prosthesis along an axis parallel to the plane of the valve annulus, wherein an upper tension arm mounted on the valve is conformationally pressure locked against supra-annular tissue, and wherein a lower tension arm mounted on the valve is conformationally pressure locked against sub-annular tissue.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. An orthogonally deliverable prosthetic heart valve, the prosthetic valve comprising:
    an outer frame defining a central channel, a first central axis extending through the central channel;
    a flow control component having an inner frame and a set of leaflets coupled to the inner frame, the flow control component disposed within the central channel and attached to the outer frame such that a second central axis extending through the flow control component is offset from the first central axis; and
    a drum including a reinforcement frame and defining at least one perforation along an area within the reinforcement frame, the drum attached to a top edge of the outer frame to cover a portion of the central channel adjacent to and outside of the inner frame of the flow control component such that the reinforcement frame is offset from the first central axis and the second central axis,
    the outer frame forming a plurality of compressible wire cells having an orientation and cell geometry that allows compression of the prosthetic valve in an axial direction parallel to each of the first central axis and the second central axis, the outer frame forming a proximal hinge point and a distal hinge point that allows folding of the prosthetic valve in a lateral direction perpendicular to the axial direction, a longitudinal axis of the prosthetic valve extending through the proximal hinge point and the distal hinge point and being perpendicular to each of the axial direction and the lateral direction,
    wherein folding and compressing the prosthetic valve places the prosthetic valve in a compressed configuration for orthogonal delivery via a delivery catheter in which the longitudinal axis of the prosthetic valve is parallel to a longitudinal axis extending through a lumen of the delivery catheter when the prosthetic valve is disposed therein.

2. The prosthetic valve of claim 1, wherein each of the compression of the prosthetic valve and the folding of the prosthetic valve is reversible, the prosthetic valve is configured to transition from the compressed configuration to an expanded configuration when the prosthetic valve is released from the delivery catheter.

3. The prosthetic valve of claim 1, wherein
    each of the inner frame and the reinforcement frame is elastically deformable from a substantially cylindrical shape to a substantially flattened shape when the prosthetic valve is folded in the lateral direction, and
    the prosthetic valve being placed in the compressed configuration when the prosthetic valve is folded in the lateral direction and compressed in the axial direction.

4. The prosthetic valve of claim 1, wherein the drum includes at least one radio-opaque marker along the reinforcement frame.

5. The prosthetic valve of claim 1, wherein the at least one perforation allowing the formation of an aperture in the area of the drum within the reinforcement frame.

6. The prosthetic valve of claim 5, wherein the flow control component is attached to the outer frame to permit blood flow in a first direction through the flow control component from an inflow end of the prosthetic valve to an outflow end of the prosthetic valve and to block blood flow through the flow control component in a second direction, opposite the first direction, and
    the aperture when formed in the drum selectively permits regurgitation blood flow in the second direction through the aperture, the first direction and the second direction being substantially parallel to the axial direction.

7. The prosthetic valve of claim 6, wherein a size of the aperture when the aperture is formed in the drum is based at least in part on a desired grade of regurgitation through the aperture, the grade of regurgitation being between 0.5 and 2.0.

8. The prosthetic valve of claim 6, further comprising:
    a cover selectively coupled to the drum about the aperture when the aperture is formed in the drum, the cover substantially sealing the drum to prevent the regurgitation blood flow in the second direction through the aperture.

* * * * *